US010370702B2

(12) United States Patent
Wu et al.

(10) Patent No.: US 10,370,702 B2
(45) Date of Patent: *Aug. 6, 2019

(54) METHODS OF MAKING OLIGONUCLEOTIDE PROBES

(71) Applicant: President and Fellows of Harvard College, Cambridge, MA (US)

(72) Inventors: Chao-ting Wu, Brookline, MA (US); Brian Beliveau, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/273,041

(22) Filed: Sep. 22, 2016

(65) Prior Publication Data

US 2017/0002402 A1    Jan. 5, 2017

Related U.S. Application Data

(62) Division of application No. 13/654,757, filed on Oct. 18, 2012, now Pat. No. 9,476,089.

(51) Int. Cl.
*C12N 15/00* (2006.01)
*C12Q 1/6811* (2018.01)
*C12Q 1/6813* (2018.01)

(52) U.S. Cl.
CPC .......... *C12Q 1/6811* (2013.01); *C12Q 1/6813* (2013.01)

(58) Field of Classification Search
CPC .................................................... C12Q 1/68
See application file for complete search history.

(56) References Cited

U.S. PATENT DOCUMENTS

| 4,230,558 | A | 10/1980 | Fulwyler |
| 4,318,846 | A | 3/1982 | Khanna et al. |
| 4,659,774 | A | 4/1987 | Webb et al. |
| 4,683,195 | A | 7/1987 | Mullis et al. |
| 4,683,202 | A | 7/1987 | Mullis |
| 4,757,141 | A | 7/1988 | Fung et al. |
| 4,811,218 | A | 3/1989 | Hunkapiller et al. |
| 4,849,336 | A | 7/1989 | Miyoshi et al. |
| 4,861,571 | A | 8/1989 | Harada et al. |
| 5,066,580 | A | 11/1991 | Lee |
| 5,091,519 | A | 2/1992 | Cruickshank |
| 5,141,813 | A | 8/1992 | Nelson |
| 5,151,507 | A | 9/1992 | Hobbs, Jr. et al. |
| 5,168,038 | A | 12/1992 | Tecott et al. |
| 5,188,934 | A | 2/1993 | Menchen et al. |
| 5,198,537 | A | 3/1993 | Huber et al. |
| 5,210,015 | A | 5/1993 | Gelfand et al. |

(Continued)

FOREIGN PATENT DOCUMENTS

| EP | 0799897 A1 | 10/1997 |
| WO | 91/17160 A1 | 11/1991 |

(Continued)

OTHER PUBLICATIONS

Albretsen et al., Anal. Biochem., 1990, pp. 40.

(Continued)

*Primary Examiner* — Aaron A Priest
(74) *Attorney, Agent, or Firm* — Banner & Witcoff, Ltd.

(57) ABSTRACT

The present invention relates to methods of making linear nucleic acid probes using rolling circle amplification methods.

10 Claims, 2 Drawing Sheets

Specification includes a Sequence Listing.

(56) References Cited

U.S. PATENT DOCUMENTS

| | | |
|---|---|---|
| 5,264,566 A | 11/1993 | Froehler et al. |
| 5,344,757 A | 9/1994 | Holtke et al. |
| 5,354,657 A | 10/1994 | Holtke et al. |
| 5,366,860 A | 11/1994 | Bergot et al. |
| 5,424,186 A | 6/1995 | Fodor et al. |
| 5,428,148 A | 6/1995 | Reddy et al. |
| 5,445,934 A | 8/1995 | Fodor et al. |
| 5,554,744 A | 9/1996 | Bhongle et al. |
| 5,574,146 A | 11/1996 | Reddy et al. |
| 5,602,244 A | 2/1997 | Caruthers et al. |
| 5,612,199 A | 3/1997 | Western et al. |
| 5,635,400 A | 6/1997 | Brenner |
| 5,688,648 A | 11/1997 | Mathies et al. |
| 5,700,637 A | 12/1997 | Southern |
| 5,700,642 A | 12/1997 | Monforte et al. |
| 5,702,888 A | 12/1997 | Holtke et al. |
| 5,739,386 A | 4/1998 | Holmes |
| 5,744,305 A | 4/1998 | Fodor et al. |
| 5,800,996 A | 9/1998 | Lee et al. |
| 5,830,655 A | 11/1998 | Monforte et al. |
| 5,847,162 A | 12/1998 | Lee et al. |
| 5,925,517 A | 7/1999 | Tyagi et al. |
| 5,959,463 A | 9/1999 | Funakura et al. |
| 5,981,179 A | 11/1999 | Lorinez et al. |
| 5,990,479 A | 11/1999 | Weiss et al. |
| 6,066,459 A | 5/2000 | Garini et al. |
| 6,124,090 A | 9/2000 | Rose et al. |
| 6,174,670 B1 | 1/2001 | Wittwer et al. |
| 6,207,392 B1 | 3/2001 | Weiss et al. |
| 6,251,303 B1 | 6/2001 | Bawendi et al. |
| 6,261,797 B1 | 7/2001 | Sorge et al. |
| 6,294,323 B1 | 9/2001 | Ullman et al. |
| 6,319,426 B1 | 11/2001 | Bawendi et al. |
| 6,322,901 B1 | 11/2001 | Bawendi et al. |
| 6,365,375 B1 | 4/2002 | Dietmaier et al. |
| 6,375,903 B1 | 4/2002 | Cerrina et al. |
| 6,391,544 B1 | 5/2002 | Salituro et al. |
| 6,423,551 B1 | 7/2002 | Weiss et al. |
| 6,426,513 B1 | 7/2002 | Bawendi et al. |
| 6,432,360 B1 | 8/2002 | Church |
| 6,444,143 B2 | 9/2002 | Bawendi et al. |
| 6,569,627 B2 | 5/2003 | Wittwer et al. |
| 6,576,291 B2 | 6/2003 | Bawendi et al. |
| 6,800,439 B1 | 10/2004 | McGall et al. |
| 6,824,866 B1 | 11/2004 | Glazer et al. |
| 6,830,890 B2 | 12/2004 | Lockhart et al. |
| 6,833,450 B1 | 12/2004 | McGall et al. |
| 2002/0045045 A1 | 4/2002 | Adams et al. |
| 2002/0081582 A1 | 6/2002 | Gao et al. |
| 2003/0017264 A1 | 1/2003 | Treadway et al. |
| 2003/0068633 A1 | 4/2003 | Belshaw et al. |
| 2003/0186226 A1 | 10/2003 | Brennan et al. |
| 2004/0106728 A1 | 6/2004 | McGall et al. |
| 2006/0281153 A1 | 12/2006 | Getts et al. |
| 2008/0318796 A1 | 12/2008 | Drmanac et al. |
| 2009/0036315 A1 | 2/2009 | Labgold et al. |
| 2009/0280538 A1* | 11/2009 | Patel ............... C12N 15/10 435/91.2 |

FOREIGN PATENT DOCUMENTS

| | | | |
|---|---|---|---|
| WO | 93/20092 A1 | 10/1993 | |
| WO | 9743404 A2 | 11/1997 | |
| WO | WO-9909216 A2 * | 2/1999 | ............ C12N 15/10 |
| WO | 02/24597 A2 | 3/2002 | |
| WO | 03/040410 A1 | 5/2003 | |
| WO | 03/046223 A1 | 6/2003 | |
| WO | 03/064027 A2 | 8/2003 | |
| WO | 03/064699 A2 | 8/2003 | |
| WO | 03/065038 A2 | 8/2003 | |
| WO | 03/066212 A2 | 8/2003 | |
| WO | 03/094026 A1 | 8/2003 | |
| WO | 03/100012 A2 | 12/2003 | |
| WO | 04/029586 A1 | 4/2004 | |
| WO | 04/031399 A2 | 4/2004 | |
| WO | 04031351 A2 | 4/2004 | |
| WO | 2007092538 A2 | 8/2007 | |

OTHER PUBLICATIONS

Aviel-Ronen et al., BMC Genomics, 2006, pp. 312, vol. 7.
Baner et al. (Signal amplification of padlock probes by rolling circle replication, Nucleic Acids Research, vol. 26, No. 22, pp. 5073-5078, 1998).
Bayani et al., Curr. Protocol. Cell Biol., 2004, 22.5.1-22.5.25.
Beaucage et al., Tetrahedron Lett., 1981.
Becker-Andre et al., Nucleic Acids Research, 1989, pp. 9437-9447.
Bernard et al., Anal. Biochem., 1999, pp. 221-228.
Brenner et al., Nat. Biotech., 2000, pp. 630.
Brenner et al., Proc. Natl. Acad. Sci., pp. 1665.
Cleary et al., Nature Methods, 2004, pp. 241.
Coen et al. (The Polymerase Chain Reaction, in Current Protocols in Molecular Biology 15.0.1-15.03, Oct. 2009).
Dahl et al. (Circle-to-circle amplification for precise and sensitive DNA analysis, PNAS, col. 101, No. 13, pp. 1548-4553, Mar. 30, 2004.
Dale et al., Proc. Nat. Acad. Sci., USA, 1973, pp. 2238-2242, vol. 70.
Danilova et al., Chromosoma, 2008, pp. 345.
Dean et al., Genome Res., 2001, pp. 1095-1099, vol. 11.
Dean et al., Proc. Natl. Acad. Sci. U.S.A., 2002, pp. 5261-5266, vol. 99.
Dejardin et al., Cell, 2009, pp. 175.
Diegelman, "Generation of Circular RNAs and Trans-Cleaving Catalytic RNAs by Rolling Transcription of Circular DNA Oligonucleotides Encoding Hairpin Ribozymes", Nucleic Acids Research, 1998, pp. 3235-3241, vol. 26.
Diviacco et al., Gene, 1992, 3013-3020.
Dressman, et al., Proc. Natl. Acad. Sci. USA, 2003, pp. 8817.
Duggan et al., "Microarrays: Making Them and Using Them in Microarray Bioinformatics", 2003, Cambridge University Press.
Duncan et al., Anal. Biochem., 1988, pp. 104.
Fransz et al., Proc. Natl. Acad. Sci. USA, 2002, pp. 14584.
Freeman et al., Biotechniques, 1999, 112-126.
Gill et al. (Nucleic Acid Isothermal Amplification Technologies—A Review, Nucleosides, Nucleotides, and Nucleic Acids, 27:224-243, 2008).
Goldkorn, Nucleic Acids Res., 1986, pp. 9171.
Greenberg et al., J. Org. Chem., 1994, 746-753.
Guatelli et al., Proc. Natl. Acad. Sci. U.S.A. 1990, pp. 1874.
Hardy et al., Nucleic Acids Research, 1994, pp. 2998-3004.
Henegariu et al., Nature Biotechnol., 2000, pp. 345.
Holmes et al., J. Org. Chem., 1997, pp. 2370-2380.
Jaffe et al., J. Biol. Chem., 2000, pp. 2619.
Kahl et al., J. Org. Chem., 1998, pp. 4870-4871.
Kahl et al., J. Org. Chem., 1999, pp. 507-510.
Kool et al., "Circular Oligonucleotides: New Concepts in Oligonucleotide Design", Annu. Rev. Biophys. Biomol. Struct., 1996, pp. 1-28, vol. 25.
Kwoh et al., Proc. Natl. Acad. Sci. 1989, pp. 1173.
Lakowicz et al., Bio Techniques, 2003, pp. 62.
Landegran et al., Science, 1988, pp. 1077-1080.
Lang et al., Nucleic Acids Res., 1988, pp. 10861.
Langdale et al., Gene, 1985, pp. 201.
Lizardi et al., Bio Technology, 1988, pp. 1197.
Mackay et al., Nucleic Acids Research, 2002, pp. 1292-1305.
Matieucci et al., J. Am. Chem. Soc., 1981, pp. 3185.
McGall et al., "Synthetic DNA Arrays in Genetic Engineering", Proc. Natl. Acad. Sci. USA, 1996, pp. 13555, vol. 20.
Mitra et al., "In Situ Localized Amplification and Contact Replication of Many Individual DNA Molecules", Nuc. Acid. Res., 1999, pp. e34, vol. 27.
Mullis et al., Cold Spring Harb. Symp. Quant. Biol., 1986, pp. 263-273, vol. 51.

(56) References Cited

OTHER PUBLICATIONS

Murray et al. (Sequence-specific cleavage of RNA by Type II restriction enzymes, Nucleic Acids Research, 2010, vol. 38, No. 22 8257-8268, Aug. 11, 2010).
Myllykangas et al. (Targeted sequencing library preparation by genomic DNA circularization, BMC Biotechnology 2011, 11:122);
Thermo Scientific (Self-circularization of Linear DNA, attached, 2012).
Nakazawa et al., Proc. Natl. Acad. Sci. U.S.A. 1994, pp. 360-364.
NCBI (PCR, attached, accessed Apr. 15, 2014).
Nunez et al. (Application of Circular Ligase to Provide Template for Rolling Circle Amplification of Low Amounts of Fragmented DNA, attached, 19th International Symposium on Human Identification, Oct. 13-16, 2008, Hollywood, California).
Olejnik et al., "Photocleavable Biotin Derivatives: A Versatile Approach for the Isolation of Biomolecules", Proc. Natl. Acad. Sci., U.S.A., 1995, pp. 7590-7594, vol. 92.
Polsky-Cynkin et al., Clin. Chem., 1985, pp. 1438.
Pon R., Methods Mol. Biol., 1993, pp. 465-496.
Promega Connections (A Quick Method for a Tailing PCR Products; attached, 2010).
Quail (DNA: Mechanical Breakage, In: Encyclopedia of Life Sciences (ELS). John Wiley & Sons, Ltd: Chichester, Nov. 15, 2010).
Ranki, et al., Gene, 1983, pp. 77.
Ried et al., Proc. Natl. Acad. Sci. USA, 1992, 1388-1392.
Roberts et al., Genes, Chrom. Cancer, 1999, pp. 241.
Schrock et al., Science, 1996, pp. 494.
Shendure et al., "Accurate Multiplex Polony Sequencing of an Evolved Bacterial Genome", Science, 2005, pp. 1728-1732, vol. 309.
Shoemaker et al., Nature Genetics, 1996, pp. 450.
Southern, Current Opin. Biol., 1998, pp. 404-410.
Speicher et al., Nature Genet., 1996, pp. 368.
Takara (DNA Ligation Kit Ver. 2.1, attached, Jul. 3, 2009)).
Telenius et al., "Degenerate Oligonucleotide-Primed PCR: General Amplification of Target DNA by a Single Degenerate Primer", Genomics, 1992, pp. 718-725, vol. 13.
Van Ness et al., Nucleic Acids Res., 1991, pp. 3345.
Vanatesan et al., J. Org. Chem., 1996, pp. 525-529.
Verma et al., Ann. Rev. Biochem., 1998, pp. 99-134.
Wheeless et al., "Flow Cytometry: Instrumentation and Data Analysis", Academic Press, 1985, pp. 21-76, New York.
Williams et al., "Amplification of Complex Gene Libraries by Emulsion PCR", Nat. Methods, 2006, pp. 545-550, vol. 3.
Williams et al., J. Biol. Chem., 2002, pp. 7790.
Wolf et al., Nucleic Acids Res., 1987, pp. 2911.
Zhang et al., "Whole Genome Amplification from a Single Cell: Implications for Genetic Analysis", Proc. Natl. Acad. Sci. U.S.A., 1992, pp. 5847-5851, vol. 89.
Zimmerman et al., Biotechniques, 1996, 268-279.

\* cited by examiner

SEQUENCE LISTING

<160> NUMBER OF SEQ ID NOS: 3

<210> SEQ ID NO 1
<211> LENGTH: 18
<212> TYPE: DNA
<213> ORGANISM: Artificial
<220> FEATURE:
<223> OTHER INFORMATION: Bridge Oligonucleotide

<400> SEQUENCE: 1
atgaggaacc cggggcag                                                 18

<210> SEQ ID NO 2
<211> LENGTH: 20

```
<212> TYPE: DNA
<213> ORGANISM: Artificial
<220> FEATURE:
<223> OTHER INFORMATION: Rolling Circle Amplification Primer
<220> FEATURE:
<221> NAME/KEY: misc_feature
<222> LOCATION: (19)..(20)
<223> OTHER INFORMATION: Phosphorothioate Bond

<400> SEQUENCE: 2
aatgaggaac ccggggcagc                                              20

<210> SEQ ID NO 3
<211> LENGTH: 20
<212> TYPE: DNA
<213> ORGANISM: Artificial
<220> FEATURE:
<223> OTHER INFORMATION: Rolling Circle Amplification Primer
<220> FEATURE:
<221> NAME/KEY: misc_feature
<222> LOCATION: (1)..(2)
<223> OTHER INFORMATION: Phosphorothioate Bond

<400> SEQUENCE: 3
aatgaggaac ccggggcagc                                              20
```

METHODS OF MAKING OLIGONUCLEOTIDE PROBES

RELATED APPLICATION DATA

This application is a divisional application which claims priority to U.S. patent application Ser. No. 13/654,757, filed on Oct. 18, 2012 and is hereby incorporated herein by reference in its entirety for all purposes.

STATEMENT OF GOVERNMENT INTERESTS

This invention was made with government support under RO1 GM085169 awarded by National Institutes of Health. The government has certain rights in the invention.

FIELD

The present invention relates in general to methods of making nucleic acids. The present invention further relates to a method of making nucleic acids that can hybridize to nucleic acid sequences of interest. The present invention further relates to a method of making nucleic acids that can hybridize to nucleic acid sequences of interest, wherein the nucleic acids included a label directly or indirectly attached to the nucleic acids. The nucleic acids can be used to locate the label at a nucleic acid sequence of interest.

BACKGROUND

Fluorescence in situ hybridization (FISH) is a powerful technology wherein nucleic acids are targeted by fluorescently labeled probes and then visualized via microscopy. FISH is a single-cell assay, making it especially powerful for the detection of rare events that might be otherwise lost in mixed or asynchronous populations of cells. In addition, because FISH is applied to fixed cell or tissue samples, it can reveal the positioning of chromosomes relative to nuclear, cytoplasmic, and even tissue structures, especially when applied in conjunction with immunofluorescent targeting of cellular components. FISH can also be used to visualize RNA, making it possible for researchers to simultaneously assess gene expression, chromosome position, and protein localization.

FISH probes are typically derived from genomic inserts subcloned into vectors such as plasmids, cosmids, and bacterial artificial chromosomes (BACs), or from flow-sorted chromosomes. These inserts and chromosomes can be used to produce probes labeled directly via nick translation or PCR in the presence of fluorophore-conjugated nucleotides or probes labeled indirectly with nucleotide-conjugated haptens, such as biotin and digoxigenin, which can be visualized with secondary detection reagents. Probe DNA is often fragmented into about 150-250 bp pieces to facilitate its penetration into fixed cells and tissues. As many genomic clones contain highly repetitive sequences, such as SINE and Alu elements, hybridization often needs to be performed in the presence of unlabeled repetitive DNA to prevent off-target hybridizations that increase background signal.

There are several limitations to clone-based FISH probes. The genomic regions that can be visualized by these probes are restricted by the availability of the clones that will serve as templates for probe production and the size of their genomic inserts, which typically range from 50-300 kb. While it is possible to target larger regions and establish banding patterns by combining probes, this approach is labor intensive and often technically difficult, as each clone needs to be amplified, purified, labeled, and optimized for hybridization separately. The hybridization efficiency of these probes is also highly variable, even among different preparations of the same probe. This variation may be a consequence of the random labeling and fragmentation steps used during probe production.

Many types of custom-synthesized oligonucleotides (oligos) have also been used as FISH probes, including DNA (14), peptide nucleic acid (PNA), and locked nucleic acid (LNA) oligos. One advantage of oligo probes is that they are designed to target a precisely defined sequence rather than relying on the isolation of a clone that is specific for the desired genomic target. Also, as these probes are typically short (about 20-50 bp) and single-stranded by nature, they efficiently diffuse into fixed cells and tissues and are unhindered by competitive hybridization between complimentary probe fragments. Recently developed methods utilizing oligo probes have allowed the visualization of single-copy viral DNA as well as individual mRNA molecules using branched DNA signal amplification or a few dozen short oligo probes and, by targeting contiguous blocks of highly repetitive sequences as a strategy to amplify signal, enabled the first FISH-based genome-wide RNAi screen. Oligo FISH probes have also been generated directly from genomic DNA using many parallel PCR reactions. However, the high cost of synthesizing oligo probes has limited their use.

The availability of complex oligo libraries produced by massively parallel synthesis has enabled a new generation of oligo-based technologies. These libraries are synthesized on a solid substrate, then amplified or chemically cleaved in order to move the library into solution. Popular applications of oligo libraries include targeted capture for next generation sequencing and custom gene synthesis. Two very recent studies have used complex libraries to visualize single-copy regions of mammalian genomes by FISH. One study used long oligos (>150 bp) as templates for PCR, and then labeled the amplification products non-specifically, while the other adapted a 75-100 bp single-stranded sequence-capture library for FISH by replacing the 5' biotin with a fluorophore.

However, methods of making nucleic acid probes for use with FISH or other methods where labeled nucleic acid probes are needed are desirable. According, one object of the present disclosure is to provide methods whereby nucleic acid sequences useful as probes are made.

SUMMARY

Embodiments of the present disclosure are directed to methods of making one or more or a plurality or set of linear nucleic acids for hybridization to target nucleic acid sequences. According to one aspect, the nucleic acid sequences are single stranded nucleic acids. According to one aspect, the nucleic acid sequences may be referred to as probes. Certain nucleic acid probes may be labeled or unlabeled. Certain nucleic acid probes may be directly labeled or indirectly labeled. According to certain aspects, nucleic acid probes may include a primary nucleic acid sequence that is non-hybridizable to a target nucleic acid sequence. According to certain aspects, the primary nucleic acid sequence is hybridizable with a secondary nucleic acid sequence. According to certain aspects, the secondary nucleic acid sequence may include a label. According to this aspect, the nucleic acid probes are indirectly labeled as the secondary nucleic acid binds to the primary nucleic acid thereby indirectly labeling the probe which hybridizes to the target nucleic acid sequence. According to certain aspects, the secondary nucleic acid sequence hybridizes with the primary nucleic acid sequence to create a recognition sequence which may be recognized or bound by a functional moiety. According to certain aspects, a plurality of nucleic acid probes are provided with each having a common primary nucleic acid sequence. That is, the primary nucleic acid sequence is common to a plurality of nucleic acid probes, such that each nucleic acid probe in the plurality has the same or substantially similar primary nucleic acid sequence. In this manner, a plurality of common secondary nucleic acid sequences are provided which hybridize to the plurality of common primary nucleic acid sequences. That is, each secondary nucleic acid sequence has the same or substantially similar nucleic acid sequence. According to one exemplary embodiment, a single primary nucleic acid sequence is provided for each of the nucleic acid probes in the plurality. Accordingly, only a single secondary nucleic acid sequence which is hybridizable to the primary nucleic acid sequence need be provided to label each of the nucleic acid probes. According to certain aspects, the common secondary nucleic acid sequences may include a common label. According to this aspect, a plurality of nucleic acid probes are provided having substantially diverse nucleic acid sequences hybridizable to different target nucleic acid sequences and where the plurality of nucleic acid probes have common primary nucleic acid sequences. Accordingly, a common secondary nucleic acid sequence having a label may be used to indirectly label each of the plurality of nucleic acid probes. According to this aspect, a single or common primary nucleic acid sequence and secondary nucleic acid sequence pair can be used to indirectly label diverse nucleic acid probe sequences. Methods using nucleic acid probes as described herein include any method where probe hybridization is useful, including but not limited to fluorescence in situ hybridization methods known to those of skill in the art or any other method where a label, such as a functional moiety, is desired to be brought to or near a target nucleic acid sequence through hybridization of the probe to the target nucleic acid sequence for detection, chemical modification, retrieving or binding to a target molecule, or providing other functions.

Methods according to the present disclosure utilize long strands of nucleic acids produced from rolling circle synthesis methods from template oligonucleotides to make many short nucleic acid strands, such as single stranded nucleic acids, useful as probes. According to one aspect, the method provides the production of many single stranded nucleic acid probes without double stranded nucleic acids being present. This avoids having to separate double stranded nucleic acids from single stranded nucleic acid probes. The long strands or "probe source strands" are divided into a plurality of individual nucleic acid probes using methods known to those of skill in the art to cleave or otherwise separate nucleotides. Accordingly, a set of single stranded probes in the substantial absence of double stranded nucleic acid may be created using the methods of the present disclosure. The probe source strands may include repetitive cleavage sites, whether designed to be at particular locations or randomly placed within the probe source strands that can be used to cleave the probe source strands into individual nucleic acid probes using methods known to those of skill in the art, such as a nuclease. According to this aspect, many individual nucleic acid probes of desired sequence and length can be made by cleaving the probe source strand at the many repetitive cleavage sites. Many individual nucleic acid probes of similar sequence and length can be made using the methods described herein. Many individual nucleic acid probes of dissimilar sequence and length can be made using the methods described herein. Many individual nucleic acid probes of random sequence and length can be made using the methods described herein. Many individual nucleic acid probes of predetermined sequence and length can be made using the methods described herein. Cleavable nucleotides are known to those of skill in the art and can be present at any desired location within the probe source strand. Methods of cleaving nucleotides at any desired location within the probe source strand are known to those of skill in the art. According to an alternate aspect, the probe source strands may be cut into many individual nucleic acid probes by mechanical shear forces and nucleic acid probes of desired length can be identified from among the sheared nucleic acid probes and obtained or otherwise isolated.

According to a certain aspect, a method making a plurality of nucleic acid probes is provided that includes contacting a circular oligonucleotide template sequence with one or more primers, a polymerase and nucleotides under conditions that form a single stranded nucleic acid, wherein the circular oligonucleotide template sequence includes one or more of a polymerase recognition site, a cleavage site, or a label addition site, and cleaving the single stranded nucleic acid to form the plurality of nucleic acid probes. According to a certain aspect, a plurality of nucleic acid probes is made according to the method.

According to a certain aspect, a method making a plurality of labeled nucleic acid probes is provided that includes contacting a circular oligonucleotide template sequence with one or more primers, a polymerase and nucleotides under conditions that form a single stranded nucleic acid, wherein the circular oligonucleotide template sequence includes one or more of a polymerase recognition site, a cleavage site, or a label addition site, cleaving the single stranded nucleic acid to form the plurality of nucleic acid probes, and attaching labels to the plurality of nucleic acid probes. According to a certain aspect, a plurality of labeled nucleic acid probes is made according to the method.

According to a certain aspect, a method of making a plurality of labeled nucleic acids is provided including the steps of contacting a circular oligonucleotide template sequence with one or more primers, a polymerase and nucleotides under conditions that form a single stranded nucleic acid having a plurality of labels attached thereto, wherein the circular oligonucleotide template sequence includes one or more of a polymerase recognition site or a cleavage site, and cleaving the single stranded nucleic acid to form the plurality of nucleic acid probes having labels attached thereto. According to a certain aspect, a plurality of labeled nucleic acid probes is made according to the method.

According to a certain aspect, a method of making a plurality of single stranded nucleic acid probes is provided including contacting a circular oligonucleotide template sequence having one or more nucleic acid probe sequences with one or more primers, a polymerase and nucleic acids under conditions that form a single stranded nucleic acid, wherein the circular oligonucleotide template sequence includes one or more of a polymerase recognition site, a cleavage site, or a label addition site, and cleaving the single stranded nucleic acid to form the plurality of single stranded nucleic acid probes, wherein the single stranded nucleic acid probes include a target hybridizing portion and a target non-hybridizing portion with the target non-hybridizing portion hybridizable with a secondary nucleic acid having a label attached thereto.

According to a certain aspect, a method of making a plurality of indirectly labeled single stranded nucleic acid probes is provided including contacting a circular oligonucleotide template sequence having one or more nucleic acid probe sequences with one or more primers, a polymerase and nucleic acids under conditions that form a single stranded nucleic acid, wherein the circular oligonucleotide template sequence includes one or more of a polymerase recognition site, a cleavage site, or a label addition site, cleaving the single stranded nucleic acid to form the plurality of single stranded nucleic acid probes, wherein the single stranded nucleic acid probes include a target hybridizing portion and a target non-hybridizing portion with the target non-hybridizing portion hybridizable with a secondary nucleic acid having a label attached thereto, and hybridizing the secondary nucleic acid to the target non-hybridizing portion of the single stranded nucleic acid probes.

BRIEF DESCRIPTION OF THE DRAWINGS

The foregoing and other features and advantages of the present invention will be more fully understood from the following detailed description of illustrative embodiments taken in conjunction with the accompanying drawing in which.

DETAILED DESCRIPTION

Figure 1:
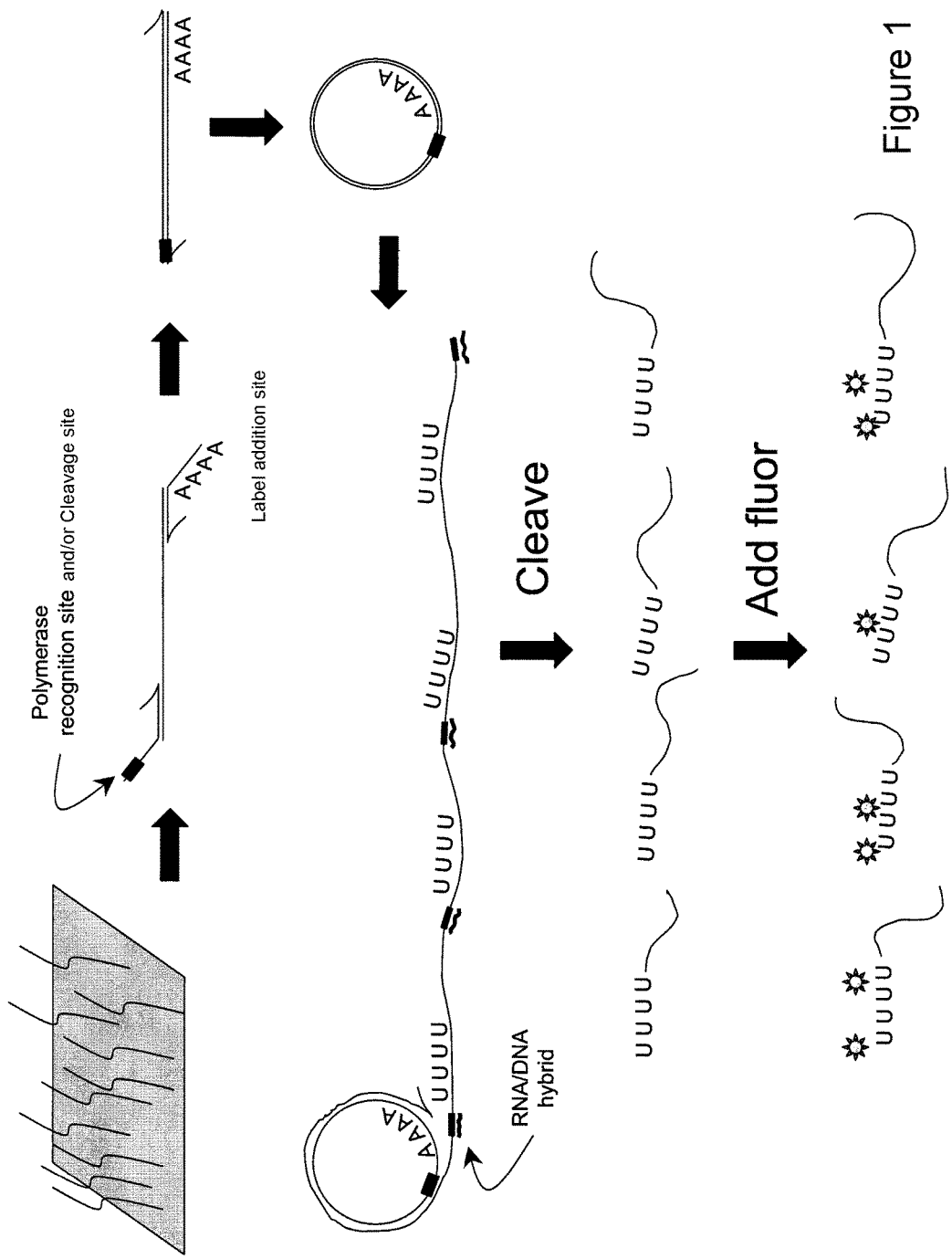
FIG. 1 is a schematic representation of aspects of the present method of making nucleic acid probes using rolling circle synthesis methods.

Terms and symbols of nucleic acid chemistry, biochemistry, genetics, and molecular biology used herein follow those of standard treatises and texts in the field, e.g., Komberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

According to embodiments of the present disclosure, a method of making a plurality of nucleic acid probes, such as linear nucleic acid probes, is provided by contacting a circular oligonucleotide template sequence with one or more primers, a polymerase and nucleic acids under conditions that form a single stranded nucleic acid. The single stranded nucleic acid may be referred to as a rolling circle amplification product. The single stranded nucleic acid may be either DNA or RNA. The single stranded nucleic acid may be labeled or unlabeled. According to one aspect, labels may be added during production of the rolling circle amplification product, by for example using labeled nucleotides during the rolling circle amplification method or other methods known to those of skill in the art. According to one aspect, labels may be added after production of the rolling circle amplification product, by for example chemical addition methods or indirect labeling by hybridization of a portion of the probe with a secondary nucleic acid sequence including a label or other methods known to those of skill in the art.

According to certain aspects, the circular oligonucleotide template sequence includes one or more of a polymerase recognition site, a cleavage site, or a label addition site, such as a detectable moiety addition site. The single stranded nucleic acid is cleaved to form the plurality of nucleic acid probes. According to one aspect, the polymerase recognition site is an RNA polymerase recognition site. According to one aspect, the polymerase recognition site is a DNA polymerase recognition site. According to one aspect, labels may be added after production of the plurality of nucleic acid probes, by for example chemical addition methods or indirect labeling by hybridization of a portion of the probe with a secondary nucleic acid sequence including a label or other methods known to those of skill in the art.

According to one aspect, the circular oligonucleotide template sequence includes a polymerase recognition site and a cleavage site. According to one aspect, the circular oligonucleotide template sequence includes a polymerase recognition site and a label addition site. According to one aspect, the circular oligonucleotide template sequence includes a cleavage site and a label addition site. According to one aspect, the circular oligonucleotide template sequence includes a polymerase recognition site, a cleavage site and a label addition site.

According to one aspect, the one or more primers include a label. According to one aspect, the one or more primers include a detectable label or moiety.

According to one aspect, cleavable moieties are cleaved using appropriate reagents or conditions known to those of skill in the art to form a plurality of nucleic acid probes, such as single stranded nucleic acid probes. Cleavable moieties can be chemically cleaved using chemical reagents or enzymatic reagents or they may be cleaved using heat or light. Cleavable moieties are well known to those of skill in the art.

According to one aspect, the single stranded nucleic acid, which is a rolling circle amplification product, is cleaved into a plurality of nucleic acid probes using an appropriate enzyme, such as an endonuclease, known to those of skill in the art. According to one aspect, the single stranded nucleic acid is cleaved into a plurality of nucleic acid probes by hybridizing an oligonucleotide to the single stranded nucleic acid, such as at the polymerase recognition site, and using an endonuclease. According to one aspect, the oligonucleotide can be DNA and the single stranded nucleic acid can be DNA. Therefore, the endonuclease is one that recognizes DNA/DNA hybrids to cleave the single stranded nucleic acid into one or more nucleic acid probes. According to one aspect, the oligonucleotide can be DNA and the single stranded nucleic acid can be RNA. Therefore, the endonuclease is one that recognizes DNA/RNA hybrids to cleave the single stranded nucleic acid into one or more nucleic acid probes. According to one aspect, the oligonucleotide can be RNA and the single stranded nucleic acid can be DNA. Therefore, the endonuclease is one that recognizes RNA/DNA hybrids to cleave the single stranded nucleic acid into one or more nucleic acid probes. According to one aspect, the oligonucleotide can be RNA and the single stranded nucleic acid can be RNA. Therefore, the endonuclease is one that recognizes RNA/RNA hybrids to cleave the single stranded nucleic acid into one or more nucleic acid probes. Endonucleases are known to those of skill in the art.

According to one aspect, the single stranded nucleic acid, which is a rolling circle amplification product, is cleaved into a plurality of nucleic acid probes using a mechanical shear force. Mechanical shear forces can be provided by commercially available blenders that use rotating blades to cut nucleic acids into smaller portions. According to this aspect, the rolling circle amplification product is cut into random length nucleic acid probes. The mechanical shear forces can be applied for a given amount of time and at a given force to prepare nucleic acid probes of desired length. For example, impacting the rolling circle amplification product with mechanical shear forces of higher energy may produce shorter nucleic acid probes. For example, impacting the rolling circle amplification product with mechanical shear forces of lower energy may produce longer nucleic acid probes.

According to one aspect, the single stranded nucleic acid is self-cleavable. According to one aspect, the single stranded nucleic acid has a sequence which can fold, orientate or otherwise assemble into an enzyme which can then cleave a nucleotide bond. An exemplary sequence is a ribozyme sequence. Such ribozyme sequences may be either RNA sequences or DNA sequences. Other sequences that are self-cleavable are known to those of skill in the art. According to one aspect, the single stranded nucleic acid has several repeating sequences which can fold, orientate or otherwise assemble into an enzyme which can then cleave a nucleotide bond, thereby producing a plurality of nucleic acids. According to one aspect, as the single stranded nucleic acid is produced using rolling circle amplification, the sequence which can fold, orientate or otherwise assemble into an enzyme, folds, orientates or otherwise assembles after production to then cleave a nucleotide bond. In this manner, nucleic acids, such as nucleic acid probes are produced as the rolling circle amplification product is being produced.

According to one aspect, a label is directly or indirectly added to the nucleic acid probes. According to one aspect, a label is directly or indirectly added to the nucleic acid probes at or through a label addition site. According to one aspect, a label is directly or indirectly added to the single stranded nucleic acid. According to one aspect, a label is directly or indirectly added to the single stranded nucleic acid at or through a label addition site. According to one aspect, a detectable moiety is directly or indirectly added to the nucleic acid probes. According to one aspect, a detectable moiety is directly or indirectly added to the nucleic acid probes through a detectable moiety addition site. According to one aspect, a detectable moiety is directly or indirectly added to the single stranded nucleic acid. According to one aspect, a detectable moiety is directly or indirectly added to the single stranded nucleic acid through a detectable moiety addition site.

With reference to FIG. 1 and according to certain embodiments of the present disclosure, a method of making a plurality of nucleic acid probes is provided including contacting an oligonucleotide template sequence with one or more first primers, a first polymerase and first nucleic acids under conditions that extend one or more hybridize primers to make a strand complementary to the oligonucleotide template sequence thereby forming a double stranded oligonucleotide to be circularized. According to an aspect, the single stranded oligonucleotide template sequence itself can be circularized (and need not be subjected to primer hybridization and extension) if, for example, the single stranded oligonucleotide template sequence has been designed to include a desired one or more of a polymerase recognition site, cleavage site or label addition site.

The term "primer" as used herein refers to an oligonucleotide which is capable of annealing to the oligonucleotide template sequence allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The primer is preferably single stranded for maximum efficiency. Preferably, the primer is an oligodeoxyribonucleotide. The primer must be sufficiently long to prime the synthesis of extension products in the presence of the oligonucleotide template sequence. The exact lengths of the primers will depend on many factors, including temperature and composition (A/T en G/C content) of primer. A pair of bi-directional primers consists of one forward and one reverse primer as commonly used in the art of DNA amplification such as in PCR amplification. The primer may include a label.

It will be understood that "primer", as used herein, may refer to more than one primer, particularly in the case where there is some ambiguity in the information regarding the terminal sequence(s) of the target region to be amplified. Hence, a "primer" includes a collection of primer oligonucleotides containing sequences representing the possible variations in the sequence or includes nucleotides which allow a typical base pairing.

The oligonucleotide primers may be prepared by any suitable method. Methods for preparing oligonucleotides of specific sequence are known in the art, and include, for example, cloning and restriction of appropriate sequences, and direct chemical synthesis. Chemical synthesis methods may include, for example, the phospho di- or tri-ester method, the diethylphosphoramidate method and the solid support method disclosed in e.g. U.S. Pat. No. 4,458,066. The primers may be labeled, if desired, by incorporating means detectable by for instance spectroscopic, fluorescence, photochemical, biochemical, immunochemical, or chemical means.

Template-dependent extension of the oligonucleotide primer(s) annealed to the oligonucleotide template sequence is catalyzed using methods known in the art such as by use of a polymerizing agent in the presence of adequate amounts of the four deoxyribonucleotide triphosphates (dATP, dGTP, dCTP and dTTP, i.e. dNTPs) or analogues, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase I or its Klenow fragment, T4 DNA polymerase, and Taq DNA polymerase. The reaction conditions for catalyzing DNA synthesis with these DNA polymerases are known in the art.

The products of the synthesis are duplex molecules including the oligonucleotide template strands and the primer extension strands.

According to one aspect, the duplex molecules of the oligonucleotide template strands and primer extension strands, may serve as template for amplification, if desired, using methods known to those of skill in the art of DNA or RNA amplification to produce amplicons of single stranded DNA or RNA or amplicons of double stranded DNA or RNA. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension result in the exponential accumulation of the target region defined by the primers.

Sufficient cycles are run to achieve the desired amount of polynucleotide containing the target region of nucleic acid. The desired amount may vary, and is determined by the function which the product polynucleotide is to serve.

The oligonucleotide template sequences may be obtained, for example, from an array of pre-synthesized oligonucleotide sequences as shown in FIG. 1. The pre-synthesized oligonucleotides may be of random sequence or non-random sequence. The pre-synthesized oligonucleotides may be of particular desired sequences designed for a particular purpose. The double stranded oligonucleotide is circularized. A rolling circle template is obtained from the circularized double stranded oligonucleotide. The rolling circle template is contacted with one or more second primers, a second polymerase and second nucleic acids under conditions that form a single stranded nucleic acid or rolling circle amplification product. The single stranded nucleic acid is cleaved to form or otherwise separated into the plurality of nucleic acid probes. The single stranded nucleic acid may contain labels as a result of the rolling circle amplification process and therefore, cleavage results in a plurality of labeled nucleic acids, such as labeled nucleic acid probes. One or more labels, such as detectable moieties, may be added to the plurality of probes at label addition sites using methods known to those of skill in the art.

According to one aspect, the single stranded nucleic acid is DNA. According to one aspect, the first polymerase or second polymerase is a DNA polymerase.

According to one aspect, the single stranded nucleic acid is RNA. According to one aspect the first polymerase or the second polymerase is an RNA polymerase.

According to one aspect, the oligonucleotide template sequence includes a polymerase recognition site. According to one aspect, the oligonucleotide template sequence includes an RNA polymerase recognition site. According to one aspect, the oligonucleotide template sequence includes a DNA polymerase recognition site.

According to one aspect, the oligonucleotide template sequence includes a cleavage site.

According to one aspect, the oligonucleotide template sequence includes a label addition site, such as a detectable label or moiety addition site.

According to one aspect, the oligonucleotide template sequence includes one or more of a polymerase recognition site, a cleavage site or a label addition site. According to one aspect, the oligonucleotide template sequence includes a polymerase recognition site and a cleavage site. According to one aspect, the oligonucleotide template sequence includes a polymerase recognition site and a label addition site. According to one aspect, the oligonucleotide template sequence includes a cleavage site and a label addition site. According to one aspect, the oligonucleotide template sequence includes a polymerase recognition site, a cleavage site and a label addition site.

According to one aspect, a polymerase recognition site is present in the strand complementary to the oligonucleotide template sequence which results from the step of extending the one or more hybridized primers to make a double stranded oligonucleotide using the oligonucleotide template sequence. According to one aspect, the one or more primers include a polymerase recognition site.

According to one aspect, a cleavage site is present in the strand complementary to the oligonucleotide template sequence which results from the step of extending the one or more hybridized primers to make a double stranded oligonucleotide using the oligonucleotide template sequence. According to one aspect, the one or more primers include a cleavage site.

According to one aspect, a label addition site is present in the strand complementary to the oligonucleotide template sequence which results from the step of extending the one or more hybridized primers to make a double stranded oligonucleotide using the oligonucleotide template sequence. According to one aspect, the one or more primers include a label addition site.

According to one aspect, one or more of a polymerase recognition site, a cleavage site or a label addition site is present in the strand complementary to the oligonucleotide template sequence which results from the step of extending the one or more hybridized primers to make a double stranded oligonucleotide using the oligonucleotide template sequence.

According to one aspect, a detectable moiety is present in the strand complementary to the oligonucleotide template sequence which results from the step of extending the one or more hybridized primers to make a double stranded oligonucleotide using the oligonucleotide template sequence. According to one aspect, the one or more primers include a detectable moiety.

Nucleic Acid

The terms "nucleic acid," "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides or ribonucleotides, or analogs thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Oligonucleotides or polynucleotides useful in the methods described herein may comprise natural nucleic acid sequences and variants thereof, artificial nucleic acid sequences, or a combination of such sequences. Oligonucleotides or polynucleotides may be single stranded or double stranded.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Oligonucleotide sequences, such as single stranded oligonucleotide sequences useful in the rolling circle amplification methods described herein, may be isolated from natural sources, synthesized or purchased from commercial sources. In certain exemplary embodiments, oligonucleotide sequences may be prepared using one or more of the phosphoramidite linkers and/or sequencing by ligation methods known to those of skill in the art. Oligonucleotide sequences may also be prepared by any suitable method, e.g., standard phosphoramidite methods such as those described herein below as well as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides, useful in the rolling circle amplification methods described herein, may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) *Proc. Natl. Acad. Sci. U.S.A.* 93:13555; *Synthetic DNA Arrays* In Genetic Engineering, Vol. 20:111, Plenum Press (1998); Duggan et al. (1999) *Nat. Genet.* S21:10; *Microarrays: Making Them and Using Them* In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 04/100012, WO 03/066212, WO 03/065038, WO 03/064699, WO 03/064027, WO 03/064026, WO 03/046223, WO 03/040410 and WO 02/24597.

Polymerase recognition sites, cleavage sites and/or label or detectable moiety addition sites may be added to the single stranded oligonucleotides during synthesis using known materials and methods.

Solid Phase Supports

In certain exemplary embodiments, one or more template nucleic acid sequences, i.e. oligonucleotide sequences, described herein are immobilized on a support (e.g., a solid and/or semi-solid support). In certain aspects, an oligonucleotide sequence can be attached to a support using one or more of the phosphoramidite linkers described herein. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. When using a support that is substantially planar, the support may be physically separated into regions, for example, with trenches, grooves, wells, or chemical barriers (e.g., hydrophobic coatings, etc.).

In certain exemplary embodiments, a support is a microarray. As used herein, the term "microarray" refers in one embodiment to a type of assay that comprises a solid phase support having a substantially planar surface on which there is an array of spatially defined non-overlapping regions or sites that each contain an immobilized nucleic acid such as a hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate create a substantially planar surface. Spatially defined sites may additionally be "addressable" in that its location and the identity of the immobilized probe at that location are known or determinable.

Oligonucleotides immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. In certain exemplary embodiments, oligonucleotides are immobilized via one or more of the cleavable linkers described herein. One or more or a plurality of cleavable moieties may also be located internally within the oligonucleotides, thereby providing sites to cleave a rolling circle amplification product into smaller nucleic acid sequences. The density of non-overlapping regions containing nucleic acids in a microarray is typically greater than 100 per $cm^2$, and more typically, greater than 1000 per $cm^2$. Microarray technology relating to nucleic acid sequences is reviewed in the following exemplary references: Schena, Editor, *Microarrays: A Practical Approach* (IRL Press, Oxford, 2000); Southern, *Current Opin. Chem. Biol.*, 2: 404-410 (1998); *Nature Genetics* Supplement, 21:1-60 (1999); and Fodor et al, U.S. Pat. Nos. 5,424,186; 5,445,934; and 5,744,305. Oligonucleotides bound to a solid support useful in the present methods are commercially available and can be designed and made using methods known to those of skill in the art.

Methods of immobilizing oligonucleotides to a support are known in the art (beads: Dressman et al. (2003) *Proc. Natl. Acad. Sci. USA* 100:8817, Brenner et al. (2000) *Nat. Biotech.* 18:630, Albretsen et al. (1990) *Anal. Biochem.* 189:40, and Lang et al. *Nucleic Acids Res.* (1988) 16:10861;

nitrocellulose: Ranki et al. (1983) *Gene* 21:77; cellulose: Goldkorn (1986) *Nucleic Acids Res.* 14:9171; polystyrene: Ruth et al. (1987) Conference of Therapeutic and Diagnostic Applications of Synthetic Nucleic Acids, Cambridge U.K.; teflon-acrylamide: Duncan et al. (1988) *Anal. Biochem.* 169:104; polypropylene: Polsky-Cynkin et al. (1985) *Clin. Chem.* 31:1438; nylon: Van Ness et al. (1991) *Nucleic Acids Res.* 19:3345; agarose: Polsky-Cynkin et al., *Clin. Chem.* (1985) 31:1438; and sephacryl: Langdale et al. (1985) *Gene* 36:201; latex: Wolf et al. (1987) *Nucleic Acids Res.* 15:2911).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

Oligonucleotide Probes

Nucleic acid sequences or oligonucleotide probes according to the present disclosure that are made from long strand nucleic acids resulting from rolling circle amplification methods may have any desired length as the rolling circle template can be designed to produced nucleic acids of any length. Accordingly, aspects of the present disclosure are directed to making a plurality or set of nucleic acid probes, such as single stranded nucleic acid probes, such as oligonucleotide paints, from rolling circle amplification products. According to this aspect, double stranded nucleic acids are substantially absent from the plurality or set of nucleic acid probes as the starting material for the single stranded probes is single stranded rolling circle amplification products. The term "probe" refers to a single-stranded oligonucleotide sequence that will recognize and form a hydrogen-bonded duplex with a complementary sequence in a target nucleic acid sequence or its cDNA derivative. The probe includes a target hybridizing nucleic acid sequence. Exemplary nucleic acid sequences may be short nucleic acids or long nucleic acids. Exemplary nucleic acid sequences include oligonucleotide paints. Exemplary nucleic acid sequences are those having between about 1 nucleotide to about 100,000 nucleotides, between about 3 nucleotides to about 50,000 nucleotides, between about 5 nucleotides to about 10,000 nucleotides, between about 10 nucleotides to about 10,000 nucleotides, between about 10 nucleotides to about 1,000 nucleotides, between about 10 nucleotides to about 500 nucleotide, between about 10 nucleotides to about 100 nucleotides, between about 10 nucleotides to about 70 nucleotides, between about 15 nucleotides to about 50 nucleotides, between about 20 nucleotides to about 60 nucleotides, between about 50 nucleotides to about 500 nucleotides, between about 70 nucleotides to about 300 nucleotides, between about 100 nucleotides to about 200 nucleotides, and all ranges or values in between whether overlapping or not. Exemplary oligonucleotide probes include between about 10 nucleotides to about 100 nucleotides, between about 10 nucleotides to about 70 nucleotides, between about 15 nucleotides to about 50 nucleotides, between about 20 nucleotides to about 60 nucleotides and all ranges and values in between whether overlapping or not.

According to one aspect, oligonucleotide probes according to the present disclosure should be capable of hybridizing to a target nucleic acid. Probes according to the present disclosure may include a label or detectable moiety as described herein. Oligonucleotides or polynucleotides may be designed, if desired, with the aid of a computer program such as, for example, DNAWorks, or Gene2Oligo.

Oligonucleotide probes according to the present disclosure need not form a perfectly matched duplex with the single stranded nucleic acid, though a perfect matched duplex is exemplary. According to one aspect, oligonucleotide probes as described herein form a stable hybrid with that of the target sequence under stringent to moderately stringent hybridization and wash conditions. If it is expected that the probes will be essentially completely complementary (i.e., about 99% or greater) to the target sequence, stringent conditions will be used. If some mismatching is expected, with the result that the probe will not be completely complementary, the stringency of hybridization may be lessened. Conditions which affect hybridization, and which select against nonspecific binding are known in the art, and are described in, for example, Sambrook et al., (2001). Generally, lower salt concentration and higher temperature increase the stringency of binding. For example, it is usually considered that stringent conditions are incubations in solutions which contain approximately 0.1×SSC, 0.1% SDS, at about 65° C. incubation/wash temperature, and moderately stringent conditions are incubations in solutions which contain approximately 1-2×SSC, 0.1% SDS and about 50°-65° C. incubation/wash temperature. Low stringency conditions are 2×SSC and about 30°-50° C.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to exemplary conditions under which a probe or primer will hybridize to its target sequence, to a detectably greater degree than other sequences (e.g. at least 2-fold over background). Other such conditions may be appropriate. Stringent conditions are sequence dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridizes to a perfectly matched probe or primer. Typically, stringent conditions will be those in which the salt concentration is less than about 1.0 M $Na^+$ ion, typically about 0.01 to 1.0 M $Na^+$ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. It is to be understood that any desired stringency and/or conditions may be employed as desired.

Nucleic acid probes according to the present disclosure may be labeled or unlabeled. Certain nucleic acid probes may be directly labeled or indirectly labeled.

Figure 2:
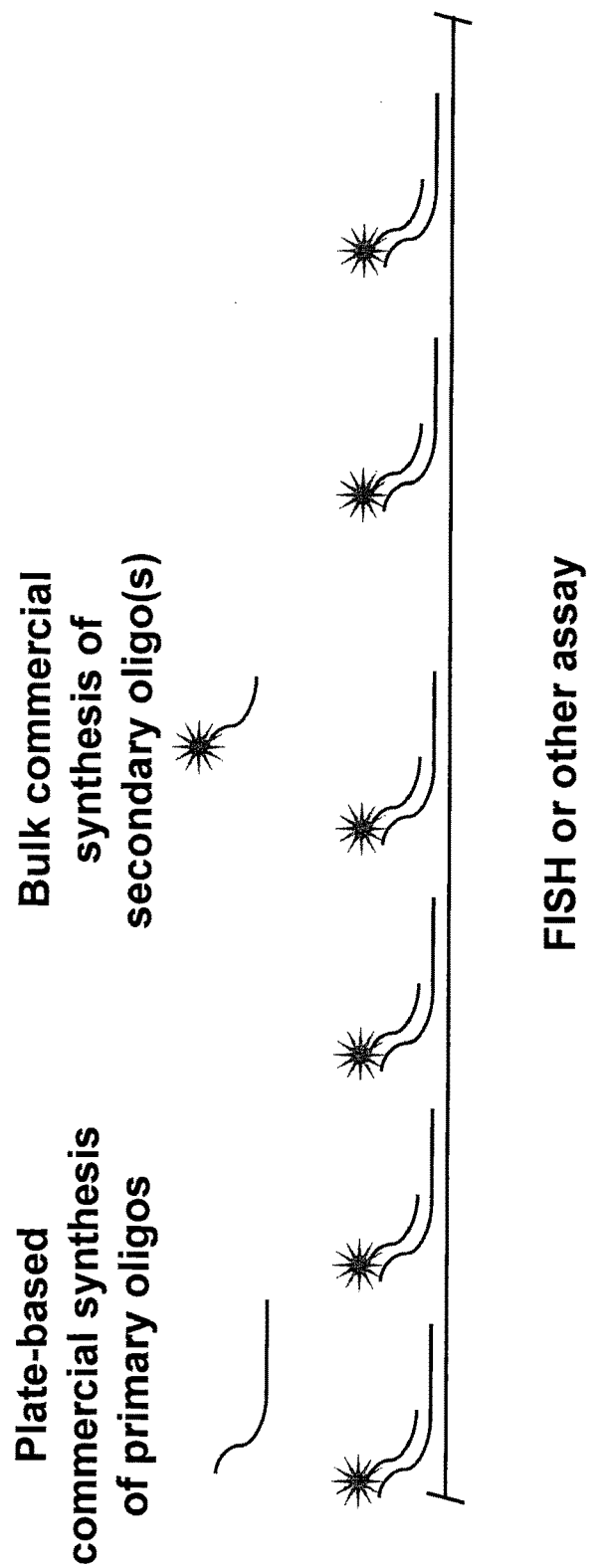
FIG. 2 is a schematic representation of aspects of the present method showing a nucleic acid probe having a target hybridizing nucleic acid sequence and a target non-hybridizing nucleic acid sequence, a labeled secondary nucleic acid sequence hybridizable with the target non-hybridizing nucleic acid sequence. Also shown in FIG. 2 is the nucleic acid probe hybridized to the target nucleic acid and the labeled secondary nucleic acid sequence hybridized to the target non-hybridizing nucleic acid sequence thereby providing an indirectly labeled probe or indirectly labeled target nucleic acid.

According to certain aspects, nucleic acid probes may include a primary nucleic acid sequence that is non-hybridizable to a target nucleic acid sequence in addition to the sequence of the probe that hybridizes to the target nucleic acid sequence. Exemplary primary nucleic acid sequences or target non-hybridizing nucleic acid sequences include between about 10 nucleotides to about 100 nucleotides, between about 10 nucleotides to about 70 nucleotides, between about 15 nucleotides to about 50 nucleotides, between about 20 nucleotides to about 60 nucleotides and all ranges and values in between whether overlapping or not. According to certain aspects, the primary nucleic acid sequence is hybridizable with one or more secondary nucleic acid sequences. According to certain aspects, the secondary nucleic acid sequence may include a label. According to this aspect, the nucleic acid probes are indirectly labeled as the secondary nucleic acid binds to the primary nucleic acid thereby indirectly labeling the probe which hybridizes to the target nucleic acid sequence. According to certain aspects, a plurality of nucleic acid probes is provided with each having a common primary nucleic acid sequence. That is, the primary nucleic acid sequence is common to a plurality of nucleic acid probes, such that each nucleic acid probe in the plurality has the same or substantially similar primary nucleic acid sequence. According to one aspect, the primary nucleic acid sequence is a single sequence species. In this manner, a plurality of common secondary nucleic acid sequences is provided which hybridize to the plurality of common primary nucleic acid sequences. That is, each secondary nucleic acid sequence has the same or substantially similar nucleic acid sequence. According to one exemplary embodiment, a single primary nucleic acid sequence is provided for each of the nucleic acid probes in the plurality. Accordingly, only a single secondary nucleic acid sequence which is hybridizable to the primary nucleic acid sequence need be provided to label each of the nucleic acid probes. According to certain aspects, the common secondary nucleic acid sequences may include a common label. According to this aspect, a plurality of nucleic acid probes are provided having substantially diverse nucleic acid sequences hybridizable to different target nucleic acid sequences and where the plurality of nucleic acid probes have common primary nucleic acid sequences. Accordingly, a common secondary nucleic acid sequence having a label may be used to indirectly label each of the plurality of nucleic acid probes. According to this aspect, a single or common primary nucleic acid sequence and secondary nucleic acid sequence pair can be used to indirectly label diverse nucleic acid probe sequences. Such an embodiment is shown in FIG. 2 where a plurality of nucleic acid probes having primary nucleic acid sequences are commercially synthesized, such as on an array. Labeled secondary nucleic acid sequences can also be commercially synthesized so that they are hybridizable with the primary nucleic acid sequences. The nucleic acid probes may be combined with the labeled secondary nucleic acids and one or more or a plurality of target nucleic acid sequences under conditions such that the nucleic acid probe or probes hybridize to the target nucleic acid sequence or sequences while the primary nucleic acid sequence is non-hybridizable to the target nucleic acid sequence or sequences. A labeled secondary nucleic acid sequence hybridizes with a corresponding primary nucleic acid sequence to indirectly label the nucleic acid probe, thereby labeling the target nucleic acid sequence. According to one aspect, the nucleic acid probes may be combined with the labeled secondary nucleic acids and one or more or a plurality of target nucleic acid sequences together in a one pot method. According to one aspect, the nucleic acid probes may be combined with the labeled secondary nucleic acids and one or more or a plurality of target nucleic acid sequences sequentially, such as the nucleic acid probes are combined with the target nucleic acid to form a mixture and then the labeled secondary nucleic acid is combined with the mixture or the nucleic acid probes are combined with the labeled secondary nucleic acids to form a mixture and then the target nucleic acid is combined with the mixture.

According to certain aspects, the primary nucleic acid sequence is modifiable with one or more labels. According to this aspect, one or more labels may be added to the primary nucleic acid sequence using methods known to those of skill in the art.

According to an additional embodiment, nucleic acid probes may include a first half of a ligand-ligand binding pair, such as biotin-avidin. Such nucleic acid probes may or may not include a primary nucleic acid sequence. The first half of a ligand-ligand binding pair may be attached directly to the nucleic acid probe. According to certain aspects, a second half of the ligand-ligand binding pair may include a label. Accordingly, the nucleic acid probe may be indirectly labeled by the use of a ligand-ligand binding pair. According to certain aspects, a common ligand-ligand binding pair may be used with a plurality of nucleic acid probes of different nucleic acid sequences. Accordingly, a single species of ligand-ligand binding pair may be used to indirectly label a plurality of different nucleic acid probe sequences. The common ligand-ligand binding pair may include a common label or a plurality of common ligand-ligand binding pairs may be labeled with different labels. Accordingly, a plurality of nucleic acid probes of different nucleic acid sequences may be labeled with a single species of label using a single species of a ligand-ligand binding pair.

According to one aspect, the primary nucleic acid sequences may include one or more subsequences that are hybridizable with one or more different secondary nucleic acid sequences. The one or more secondary nucleic acid sequences may include one or more subsequences that hybridize with one or more tertiary nucleic acid sequences, and so on. Each of the primary nucleic acid sequences, the secondary nucleic acid sequences, the tertiary nucleic acid sequences and so on may be directly labeled with a label or may be indirectly labeled with a label. In this manner, an exponential labeling of the nucleic acid probe can be achieved.

A primer according to the present disclosure includes oligonucleotide sequences that are capable of hybridizing to a template nucleic acid sequence and being extended along the length of the template nucleic acid sequence in the presence of a polymerase and nucleotides. Polymerases include those known to those of skill in the art useful for extending primers and in amplification protocols. A polymerase recognition site according to the present disclosure includes a site on a nucleic acid at which a polymerase initially binds to begin extension of a primer along the length of a nucleic acid template. Polymerase recognitions sites are known to those of skill in the art as are the polymerases which bind to such polymerase recognition sites.

Cleavable Moieties

One or more or a plurality of cleavable moieties or cleavage sites may be present within the nucleic acid sequences described herein including the oligonucleotide template sequence, the double stranded nucleic acid sequence formed from the oligonucleotide template sequence, the circular oligonucleotide template sequence formed from the double stranded nucleic acid sequence or the rolling circle amplification product form the circular oligonucleotide template sequence. A cleavage site according to the present disclosure includes cleavable nucleotide moieties also referred to as cleavable linkages which are used to separate one part of a nucleic acid from another part of a nucleic acid. Cleavable moieties are known to those of skill in the art and include chemically scissile internucleosidic linkages which may be cleaved by treating them with chemicals or subjecting them to oxidizing or reducing environments. Such cleavable moieties include phosphorothioate, phosphorothiolate which can be cleaved by various metal ions such as solutions of silver nitrate. Such cleavable moieties include phosphoroamidate which can be cleaved in acidic conditions such as solutions including acetic acid. A suitable chemical that can cleave a linkage includes a chemical that can cleave a bridged-phosphorothioate linkage and can remove a phosphoramidite linker from a nucleotide and/or oligonucleotide, leaving a free phosphate group on the nucleotide and/or oligonucleotide at the cleavage site. Suitable chemicals include, but are not limited to $AgNO_3$, $AgCH_3COO$, $AgBrO_3$, $Ag_2SO_4$, or any compound that delivers $Ag^{2+}$, $HgCl_2$, $I_2$, $Br_2$, $I^-$, $Br^-$ and the like.

Cleavable moieties also include those that can be cleaved by nucleases known to those of skill in the art. Such nucleases include restriction endonucleases such as Type I, Type II, Type III and Type IV, endonucleases such as endonucleases I-VIII, ribonucleases and other nucleases such as enzymes with AP endonuclease activity, enzymes with AP lyase activity and enzymes with glycosylase activity such as uracil DNA glycosylase.

Cleavable moieties also include those capable of being cleaved by light of a certain wavelength. Such cleavable moieties are referred to as photolabile linkages and are disclosed in Olejnik et al., Photocleavable biotin derivatives: a versatile approach for the isolation of biomolecules, *Proc. Natl. Acad. Sci. U.S.A.*, vol. 92, p. 7590-7594 (1995). Such photocleavable linkers can be cleaved by UV illumination between wavelengths of about 275 to about 375 nm for a period of a few seconds to 30 minutes, such as about one minute. Exemplary wavelengths include between about 300 nm to about 350 nm.

Certain nucleotides, such as dGTP, dCTP and dTTP could also be reacted before being incorporated for use as a cleavable linkage, making them specifically sensitive to further cleavage by nucleases or chemicals. According to one aspect, one or multiple deoxyguanosines in a given template non-hybridizing nucleic acid can be oxidized to 8-oxo-deoxyguanosine by 2-nitropropane, before being added to the sequencing reaction, and subsequently cleaved using an 8-oxoguanine DNA glycosylase (e.g. Fpg, hOGG1). Similarly, deoxycytosines can be pre-reacted to form 5-hydroxycytosine, using bisulfite or nitrous acid, which can then be processed by certain DNA-glycosylase, such as hNEIL1. Other nucleotides which can be cleaved include uracil, deoxyuridine, inosine and deoxyinosine.

Additional embodiments include nucleotides that may be cleaved in a two-step method such as by a first step that modifies the nucleotide making it more susceptible to cleavage and then a second step where the nucleotide is cleaved. Such systems include the USER system (commercially available from Enzymatics (#Y918L) or New England Biolabs (#M5505L) which is typically a combination of UDG and Endonuclease VIII, although other endonucleases could be used. Enzymes UDG and endonuclease are commercially available. In addition, modified nucleotides may be cleavable nucleotides where a feature of the nucleotide has been modified, such as a bond, so as to facilitate cleavage. Examples include an abasic base, an apyrimidic base, an apurinic base, phospohrothioate, phosphorothiolate and oxidized bases such as deoxyguanosines which can be oxidized to 8-oxo-deoxyguanosine.

Accordingly, internucleotide bonds may be cleaved by chemical, thermal, or light based cleavage. Exemplary chemically cleavable internucleotide linkages for use in the methods described herein include, for example, β-cyano ether, 5'-deoxy-5'-aminocarbamate, 3'deoxy-3'-aminocarbamate, urea, 2'cyano-3',5'-phosphodiester, 3'-(S)-phosphorothioate, 5'-(S)-phosphorothioate, 3'-(N)-phosphoramidate, 5'-(N)-phosphoramidate, α-amino amide, vicinal diol, ribonucleoside insertion, 2'-amino-3',5'-phosphodiester, allylic sulfoxide, ester, silyl ether, dithioacetal, 5'-thio-furmal, α-hydroxy-methyl-phosphonic bisamide, acetal, 3'-thio-furmal, methylphosphonate and phosphotriester. Internucleoside silyl groups such as trialkylsilyl ether and dialkoxysilane are cleaved by treatment with fluoride ion. Base-cleavable sites include β-cyano ether, 5'-deoxy-5'-aminocarbamate, 3'-deoxy-3'-aminocarbamate, urea, 2'-cyano-3',5'-phosphodiester, 2'-amino-3',5'-phosphodiester, ester, and ribose. Thio-containing internucleotide bonds such as 3'-(S)-phosphorothioate and 5'-(S)-phosphorothioate are cleaved by treatment with silver nitrate or mercuric chloride. Acid cleavable sites include 3'-(N)-phosphoramidate, 5'-(N)-phosphoramidate, dithioacetal, acetal and phosphonic bisamide. An α-aminoamide internucleoside bond is cleavable by treatment with isothiocyanate, and titanium may be used to cleave a 2'-amino-3',5'-phosphodiester-O-ortho-benzyl internucleoside bond. Vicinal diol linkages are cleavable by treatment with periodate. Thermally cleavable groups include allylic sulfoxide and cyclohexene while photo-labile linkages include nitrobenzylether and thymidine dimer. Methods synthesizing and cleaving nucleic acids containing chemically cleavable, thermally cleavable, and photo-labile groups are described for example, in U.S. Pat. No. 5,700,642.

Accordingly, internucleotide bonds may be cleaved using enzymatic cleavage. Nucleic acid sequences described herein may be designed to include a restriction endonuclease cleavage site. A nucleic acid may be contacted with a restriction endonuclease to result in cleavage. A wide variety of restriction endonucleases having specific binding and/or cleavage sites are commercially available, for example, from New England Biolabs (Ipswich, Mass.). In various embodiments, restriction endonucleases that produce 3' overhangs, 5' overhangs or blunt ends may be used. When using a restriction endonuclease that produces an overhang, an exonuclease (e.g., $RecJ_f$, Exonuclease I, Exonuclease T, $S_1$ nuclease, $P_1$ nuclease, mung bean nuclease, CEL I nuclease, etc.) may be used to produce blunt ends. In an exemplary embodiment, an orthogonal primer/primer binding site that contains a binding and/or cleavage site for a type IIS restriction endonuclease may be used to remove the temporary orthogonal primer binding site.

As used herein, the term "restriction endonuclease recognition site" is intended to include, but is not limited to, a particular nucleic acid sequence to which one or more restriction enzymes bind, resulting in cleavage of a DNA molecule either at the restriction endonuclease recognition sequence itself, or at a sequence distal to the restriction endonuclease recognition sequence. Restriction enzymes include, but are not limited to, type I enzymes, type II enzymes, type IIS enzymes, type III enzymes and type IV enzymes. The REBASE database provides a comprehensive database of information about restriction enzymes, DNA methyltransferases and related proteins involved in restriction-modification. It contains both published and unpublished work with information about restriction endonuclease recognition sites and restriction endonuclease cleavage sites, isoschizomers, commercial availability, crystal and sequence data (see Roberts et al. (2005) *Nucl. Acids Res.* 33:D230, incorporated herein by reference in its entirety for all purposes).

In certain aspects, primers of the present invention include one or more restriction endonuclease recognition sites that enable type IIS enzymes to cleave the nucleic acid several base pairs 3' to the restriction endonuclease recognition sequence. As used herein, the term "type IIS" refers to a restriction enzyme that cuts at a site remote from its recognition sequence. Type IIS enzymes are known to cut at a distances from their recognition sites ranging from 0 to 20 base pairs. Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.). Information about the recognition sites, cut sites and conditions for digestion using type IIs endonucleases may be found, for example, on the Worldwide web at neb.com/nebecomm/enzymefindersearch bytypeIIs.asp). Restriction endonuclease sequences and restriction enzymes are well known in the art and restriction enzymes are commercially available (New England Biolabs, Ipswich, Mass.).

According to certain aspects, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al., *Ann. Rev. Biochem.* 67:99-134 (1998); U.S. Pat. Nos. 5,739,386, 5,700,642 and 5,830,655; and U.S. Patent Publication Nos. 2003/0186226 and 2004/0106728).

The cleavable site may be located along the oligonucleotide backbone, for example, a modified 3'-5' internucleotide linkage in place of one of the phosphodiester groups, such as ribose, dialkoxysilane, phosphorothioate, and phosphoramidate internucleotide linkage. The cleavable oligonucleotide analogs may also include a substituent on, or replacement of, one of the bases or sugars, such as 7-deazaguanosine, 5-methylcytosine, inosine, uridine, and the like.

In one embodiment, cleavable sites contained within the modified oligonucleotide may include chemically cleavable groups, such as dialkoxysilane, 3'-(S)-phosphorothioate, 5'-(S)-phosphorothioate, 3'-(N)-phosphoramidate, 5'-(N)phosphoramidate, and ribose. Synthesis and cleavage conditions of chemically cleavable oligonucleotides are described in U.S. Pat. Nos. 5,700,642 and 5,830,655. For example, depending upon the choice of cleavable site to be introduced, either a functionalized nucleoside or a modified nucleoside dimer may be first prepared, and then selectively introduced into a growing oligonucleotide fragment during the course of oligonucleotide synthesis. Selective cleavage of the dialkoxysilane may be effected by treatment with fluoride ion. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide.

In another embodiment, a non-cleavable hydroxyl linker may be converted into a cleavable linker by coupling a special phosphoramidite to the hydroxyl group prior to the phosphoramidite or H-phosphonate oligonucleotide synthesis as described in U.S. Patent Application Publication No. 2003/0186226. The cleavage of the chemical phosphorylation agent at the completion of the oligonucleotide synthesis yields an oligonucleotide bearing a phosphate group at the 3' end. The 3'-phosphate end may be converted to a 3' hydroxyl end by a treatment with a chemical or an enzyme, such as alkaline phosphatase, which is routinely carried out by those skilled in the art.

In another embodiment, the cleavable linking moiety may be a TOPS (two oligonucleotides per synthesis) linker (see e.g., PCT publication WO 93/20092). For example, the TOPS phosphoramidite may be used to convert a non-cleavable hydroxyl group on the solid support to a cleavable linker. A preferred embodiment of TOPS reagents is the Universal TOPS™ phosphoramidite. Conditions for Universal TOPS™ phosphoramidite preparation, coupling and cleavage are detailed, for example, in Hardy et al. *Nucleic Acids Research* 22(15):2998-3004 (1994). The Universal TOPS™ phosphoramidite yields a cyclic 3' phosphate that may be removed under basic conditions, such as the extended ammonia and/or ammonia/methylamine treatment, resulting in the natural 3' hydroxy oligonucleotide.

In another embodiment, a cleavable linking moiety may be an amino linker. The resulting oligonucleotides bound to the linker via a phosphoramidate linkage may be cleaved with 80% acetic acid yielding a 3'-phosphorylated oligonucleotide.

In another embodiment, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al., *J. Org. Chem.* 61:525-529 (1996), Kahl et al., *J. Org. Chem.* 64:507-510 (1999), Kahl et al., *J. Org. Chem.* 63:4870-4871 (1998), Greenberg et al., *J. Org. Chem.* 59:746-753 (1994), Holmes et al., *J. Org. Chem.* 62:2370-2380 (1997), and U.S. Pat. No. 5,739,386. Ortho-nitrobenzyl-based linkers, such as hydroxymethyl, hydroxyethyl, and Fmoc-aminoethyl carboxylic acid linkers, may also be obtained commercially.

Labels

A label according to the present disclosure includes a functional moiety directly or indirectly attached or conjugated to a nucleic acid which provides a desired function. According to certain aspects, a label may be used for detection. Detectable labels or moieties are known to those of skill in the art. According to certain aspects, a label may be used to retrieve a particular molecule. Retrievable labels or moieties are known to those of skill in the art. According to certain aspects, a label may be used to target a particular molecule to a target nucleic acid of interest for a desired function. Targeting labels or moieties are known to those of skill in the art. According to certain aspects, a label may be used to react with a target nucleic acid of interest. Reactive labels or moieties are known to those of skill in the art. According to certain aspects, a label may be an antibody, ligand, hapten, radioisotope, therapeutic agent and the like.

As used herein, the term "retrievable moiety" refers to a moiety that is present in or attached to a polynucleotide that can be used to retrieve a desired molecule or factors bound to a desired molecule (e.g., one or more factors bound to a targeting moiety).

As used herein, the term "targeting moiety" refers to a moiety that is present in or attached to a polynucleotide that can be used to specifically and/or nonspecifically bind one or more factors that associate with, modify or otherwise interact with a nucleic acid sequence of interest (e.g., DNA (e.g., nuclear, mitochondrial, transfected and the like) and/or RNA), including, but not limited to, a protein, a peptide, a DNA sequence, an RNA sequence, a carbohydrate, a lipid, a chemical moiety or the like at or near the nucleotide sequence of interest to which the polynucleotide has hybridized. In certain aspects, factors that associate with a nucleic acid sequence of interest include, but are not limited to histone proteins (e.g., H1, H2A, H2B, H3, H4 and the like, including monomers and oligomers (e.g., dimers, tetramers, octamers and the like)) scaffold proteins, transcription factors, DNA binding proteins, DNA repair factors, DNA modification proteins (e.g., acetylases, methylases and the like).

In other aspects, factors that associate with, modify or otherwise interact with a nucleic acid sequence of interest are proteins including, but not limited to, proteins that are involved with gene regulation such as, e.g., proteins associated with chromatin (See, e.g., Dejardin and Kingston (2009) *Cell* 136:175), proteins that regulate (upregulate or downregulate) methylation, proteins that regulate (upregulate or downregulate) acetylation, proteins that regulate (upregulate or downregulate) histone acetylation, proteins that regulate (upregulate or downregulate) transcription, proteins that regulate (upregulate or downregulate) post-transcriptional regulation, proteins that regulate (upregulate or downregulate) RNA transport, proteins that regulate (upregulate or downregulate) mRNA degradation, proteins that regulate (upregulate or downregulate) translation, proteins that regulate (upregulate or downregulate) post-translational modifications and the like.

In certain aspects, a targeting and/or retrievable moiety is activatable. As used herein, the term "activatable" refers to a targeting and/or retrievable moiety that is inert (i.e., does not bind a target) until activated (e.g., by exposure of the activatable, targeting and/or retrievable moiety to light, heat, one or more chemical compounds or the like). In other aspects, a targeting and/or retrievable moiety can bind one or more targets without the need for activation of the targeting and/or retrievable moiety. Exemplary methods for attaching proteins, lipids, carbohydrates, nucleic acids and the like are known to those of skill in the art. In certain aspects, a targeting moiety can be a non-targeting moiety that is cross-linked or otherwise modified to bind one or more factors that associate with, modify or otherwise interact with a nucleic acid sequence.

In certain exemplary embodiments, a targeting moiety, a retrievable moiety and/or polynucleotide has a detectable label bound thereto. As used herein, the term "detectable label" refers to a label that can be used to identify a target (e.g., a factor associated with a nucleic acid sequence of interest, a chromosome or a sub-chromosomal region). Typically, a detectable label is attached to the 3'- or 5'-end of a polynucleotide. Alternatively, a detectable label is attached to an internal portion of an oligonucleotide. Detectable labels may vary widely in size and compositions; the following references provide guidance for selecting oligonucleotide tags appropriate for particular embodiments: Brenner, U.S. Pat. No. 5,635,400; Brenner et al., *Proc. Natl. Acad. Sci.*, 97: 1665; Shoemaker et al. (1996) *Nature Genetics*, 14:450; Morris et al., EP Patent Pub. 0799897A1; Wallace, U.S. Pat. No. 5,981,179; and the like.

Methods for incorporating detectable labels into nucleic acid probes are well known. Typically, detectable labels (e.g., as hapten- or fluorochrome-conjugated deoxyribonucleotides) are incorporated into a nucleic acid, such as a nucleic acid probe during a polymerization or amplification step, e.g., by PCR, nick translation, random primer labeling, terminal transferase tailing (e.g., one or more labels can be added after cleavage of the primer sequence), and others (see Ausubel et al., 1997, Current Protocols In Molecular Biology, Greene Publishing and Wiley-Interscience, New York).

In certain aspects, a suitable targeting moiety, retrievable moiety or detectable label includes, but is not limited to, a capture moiety such as a hydrophobic compound, an oligonucleotide, an antibody or fragment of an antibody, a protein, a peptide, a chemical cross-linker, an intercalator, a molecular cage (e.g., within a cage or other structure, e.g., protein cages, fullerene cages, zeolite cages, photon cages, and the like), or one or more elements of a capture pair, e.g., biotin-avidin, biotin-streptavidin, NHS-ester and the like, a thioether linkage, static charge interactions, van der Waals forces and the like (See, e.g., Holtke et al., U.S. Pat. Nos. 5,344,757; 5,702,888; and 5,354,657; Huber et al., U.S. Pat. No. 5,198,537; Miyoshi, U.S. Pat. No. 4,849,336; Misiura and Gait, PCT publication WO 91/17160). In certain aspects, a suitable targeting label, retrievable label or detectable label is an enzyme (e.g., a methylase and/or a cleaving enzyme). In one aspect, an antibody specific against the enzyme can be used to retrieve or detect the enzyme and accordingly, retrieve or detect an oligonucleotide sequence or factor attached to the enzyme. In another aspect, an antibody specific against the enzyme can be used to retrieve or detect the enzyme and, after stringent washes, retrieve or detect a factor or first oligonucleotide sequence that is hybridized to a second oligonucleotide sequence having the enzyme attached thereto.

Biotin, or a derivative thereof, may be used as an oligonucleotide label (e.g., as a targeting moiety, retrievable moiety and/or a detectable label), and subsequently bound by a avidin/streptavidin derivative (e.g., detectably labelled, e.g., phycoerythrin-conjugated streptavidin), or an anti-biotin antibody (e.g., a detectably labelled antibody). Digoxigenin may be incorporated as a label and subsequently bound by a detectably labelled anti-digoxigenin antibody (e.g., a detectably labelled antibody, e.g., fluoresceinated anti-digoxigenin). An aminoallyl-dUTP residue may be incorporated into an oligonucleotide and subsequently coupled to an N-hydroxy succinimide (NHS) derivatized fluorescent dye. In general, any member of a conjugate pair may be incorporated into a retrievable moiety and/or a detectable label provided that a detectably labelled conjugate partner can be bound to permit detection. As used herein, the term antibody refers to an antibody molecule of any class, or any sub-fragment thereof, such as an Fab.

Other suitable labels (targeting moieties, retrievable moieties and/or detectable labels) include, but are not limited to, fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for reaction, retrieval and/or detection: biotin/ α-biotin, digoxigenin/α-digoxigenin, dinitrophenol (DNP)/ α-DNP, 5-Carboxyfluorescein (FAM)/α-FAM.

Additional suitable labels (targeting moieties, retrievable moieties and/or detectable labels) include, but are not limited to, chemical cross-linking agents. Cross-linking agents typically contain at least two reactive groups that are reactive towards numerous groups, including, but not limited to, sulfhydryls and amines, and create chemical covalent bonds between two or more molecules. Functional groups that can be targeted with cross-linking agents include, but are not limited to, primary amines, carboxyls, sulfhydryls, carbohydrates and carboxylic acids. Protein molecules have many of these functional groups and therefore proteins and peptides can be readily conjugated using cross-linking agents. Cross-linking agents are well known in the art and are commercially available (Thermo Scientific (Rockford, Ill.)).

A detectable moiety, label or reporter can be used to detect a nucleic acid or nucleic acid probe as described herein. Oligonucleotide probes or nucleic acid probes described herein can be labeled in a variety of ways, including the direct or indirect attachment of a detectable moiety such as a fluorescent moiety, hapten, colorimetric moiety and the like. A location where a label may be attached is referred to herein as a label addition site or detectable moiety addition site and may include a nucleotide to which the label is capable of being attached. One of skill in the art can consult references directed to labeling DNA. Examples of detectable moieties include various radioactive moieties, enzymes, prosthetic groups, fluorescent markers, luminescent markers, bioluminescent markers, metal particles, protein-protein binding pairs, protein-antibody binding pairs and the like. Examples of fluorescent moieties include, but are not limited to, yellow fluorescent protein (YFP), green fluorescence protein (GFP), cyan fluorescent protein (CFP), umbelliferone, fluorescein, fluorescein isothiocyanate, rhodamine, dichlorotriazinylamine fluorescein, cyanines, dansyl chloride, phycocyanin, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Identifiable markers also include radioactive compounds such as $^{125}I$, $^{35}S$, $^{14}C$, or $^{3}H$. Identifiable markers are commercially available from a variety of sources.

Fluorescent labels and their attachment to nucleotides and/or oligonucleotides are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); and Wetmur, *Critical Reviews in Biochemistry and Molecular Biology*, 26:227-259 (1991). Particular methodologies applicable to the invention are disclosed in the following sample of references: U.S. Pat. Nos. 4,757,141, 5,151,507 and 5,091,519. In one aspect, one or more fluorescent dyes are used as labels for labeled target sequences, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847, 162 (4,7-dichlororhodamine dyes); U.S. Pat. No. 4,318,846 (ether-substituted fluorescein dyes); U.S. Pat. No. 5,800,996 (energy transfer dyes); Lee et al.; U.S. Pat. No. 5,066,580 (xanthine dyes); U.S. Pat. No. 5,688,648 (energy transfer dyes); and the like. Labeling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHODAMINE GREEN™-5-UTP, ALEXA FLUOR™ 488-5-UTP, LEXA FLUOR™ 546-14-UTP (Molecular Probes, Inc. Eugene, Oreg.) and the like. Alternatively, the above fluorophores and those mentioned herein may be added during oligonucleotide synthesis using for example phosphoroamidite or NHS chemistry. Protocols are known in the art for custom synthesis of nucleotides having other fluorophores (See, Henegariu et al. (2000) *Nature Biotechnol.* 18:345). 2-Aminopurine is a fluorescent base that can be incorporated directly in the oligonucleotide sequence during its synthesis. Nucleic acid could also be stained, a priori, with an intercalating dye such as DAPI, YOYO-1, ethidium bromide, cyanine dyes (e.g. SYBR Green) and the like.

Other fluorophores available for post-synthetic attachment include, but are not limited to, ALEXA FLUOR™ 350, ALEXA FLUOR™ 405, ALEXA FLUOR™ 430, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, Pacific Orange, rhodamine 6G, rhodamine green, rhodamine red, tetramethyl rhodamine, Texas Red (available from Molecular Probes, Inc., Eugene, Oreg.), Cy2, Cy3, Cy3.5, Cy5, Cy5.5, Cy7 (Amersham Biosciences, Piscataway, N.J.) and the like. FRET tandem fluorophores may also be used, including, but not limited to, PerCP-Cy5.5, PE-Cy5, PE-Cy5.5, PE-Cy7, PE-Texas Red, APC-Cy7, PE-Alexa dyes (610, 647, 680), APC-Alexa dyes and the like.

FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes. Metallic silver or gold particles may be used to enhance signal from fluorescently labeled nucleotide and/or oligonucleotide sequences (Lakowicz et al. (2003) BioTechniques 34:62).

Biotin, or a derivative thereof, may also be used as a label on a nucleotide and/or an oligonucleotide sequence, and subsequently bound by a detectably labeled avidin/streptavidin derivative (e.g. phycoerythrin-conjugated streptavidin), or a detectably labeled anti-biotin antibody. Biotin/avidin is an example of a ligand-ligand binding pair. An antibody/antigen binging pair may also be used with methods described herein. Other ligand-ligand binding pairs or conjugate binding pairs are well known to those of skill in the art. Digoxigenin may be incorporated as a label and subsequently bound by a detectably labeled anti-digoxigenin antibody (e.g. fluoresceinated anti-digoxigenin). An aminoallyl-dUTP or aminohexylacrylamide-dCTP residue may be incorporated into an oligonucleotide sequence and subsequently coupled to an N-hydroxy succinimide (NHS) derivatized fluorescent dye. In general, any member of a conjugate pair may be incorporated into a detection oligonucleotide provided that a detectably labeled conjugate partner can be bound to permit detection. As used herein, the term antibody refers to an antibody molecule of any class, or any sub-fragment thereof, such as an Fab.

Other suitable labels for an oligonucleotide sequence may include fluorescein (FAM, FITC), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM.

In certain exemplary embodiments, a nucleotide and/or an oligonucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, PCT publication WO 91/17160 and the like. Many different hapten-capture agent pairs are available for use. Exemplary haptens include, but are not limited to, biotin, des-biotin and other derivatives, dinitrophenol, dansyl, fluorescein, CY5, digoxigenin and the like. For biotin, a capture agent may be avidin, streptavidin, or antibodies. Antibodies may be used as capture agents for the other haptens (many dye-antibody pairs being commercially available, e.g., Molecular Probes, Eugene, Oreg.).

According to certain aspects, detectable moieties described herein are spectrally resolvable. "Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in *Flow Cytometry: Instrumentation and Data Analysis* (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

In certain embodiments, the detectable moieties can provide higher detectability when used with an electron microscope, compared with common nucleic acids. Moieties with higher detectability are often in the group of metals and organometals, such as mercuric acetate, platinum dimethylsulfoxide, several metal-bipyridyl complexes (e.g. osmium-bipy, ruthenium-bipy, platinum-bipy). While some of these moieties can readily stain nucleic acids specifically, linkers can also be used to attach these moieties to a nucleic acid. Such linkers added to nucleotides during synthesis are acrydite- and a thiol-modified entities, amine reactive groups, and azide and alkyne groups for performing click chemistry. Some nucleic acid analogs are also more detectable such as gamma-adenosine-thiotriphosphate, iododeoxycytidine-triphosphate, and metallonucleosides in general (see Dale et al., Proc. Nat. Acad. Sci. USA, Vol. 70, No. 8, pp. 2238-2242 (1973)). The modified nucleotides are added during synthesis. Synthesis may refer by example to solid support synthesis of oligonucleotides. In this case, modified nucleic acids, which can be a nucleic acid analog, or a nucleic acid modified with a detectable moiety, or with an attachment chemistry linker, are added one after each other to the nucleic acid fragments being formed on the solid support, with synthesis by phosphoramidite being the most popular method. Synthesis may also refer to the process performed by a polymerase while it synthesizes the complementary strands of a nucleic acid template. Certain DNA polymerases are capable of using and incorporating nucleic acids analogs, or modified nucleic acids, either modified with a detectable moiety or an attachment chemistry linker to the complementary nucleic acid template.

Detection method(s) used will depend on the particular detectable labels used in the reactive labels, retrievable labels and/or detectable labels. In certain exemplary embodiments, target nucleic acids such as chromosomes and sub-chromosomal regions of chromosomes during various phases of the cell cycle including, but not limited to, interphase, preprophase, prophase, prometaphase, metaphase, anaphase, telophase and cytokinesis, having one or more reactive labels, retrievable labels, or detectable labels bound thereto by way of the probes described herein may be selected for and/or screened for using a microscope, a spectrophotometer, a tube luminometer or plate luminometer, x-ray film, a scintillator, a fluorescence activated cell sorting (FACS) apparatus, a microfluidics apparatus or the like.

As used herein, the term "chromosome" refers to the support for the genes carrying heredity in a living cell, including DNA, protein, RNA and other associated factors. The conventional international system for identifying and numbering the chromosomes of the human genome is used herein. The size of an individual chromosome may vary within a multi-chromosomal genome and from one genome to another. A chromosome can be obtained from any species. A chromosome can be obtained from an adult subject, a juvenile subject, an infant subject, from an unborn subject (e.g., from a fetus, e.g., via prenatal test such as amniocentesis, chorionic villus sampling, and the like or directly from the fetus, e.g., during a fetal surgery) from a biological sample (e.g., a biological tissue, fluid or cells (e.g., sputum, blood, blood cells, tissue or fine needle biopsy samples, urine, cerebrospinal fluid, peritoneal fluid, and pleural fluid, or cells therefrom) or from a cell culture sample (e.g., primary cells, immortalized cells, partially immortalized cells or the like). In certain exemplary embodiments, one or more chromosomes can be obtained from one or more genera including, but not limited to, *Homo*, *Drosophila*,

*Caenorhabiditis, Danio, Cyprinus, Equus, Canis, Ovis, Ocorynchus, Salmo, Bos, Sus, Gallus, Solanum, Triticum, Oryza, Zea, Hordeum, Musa, Avena, Populus, Brassica, Saccharum* and the like.

When fluorescently labeled targeting moieties, retrievable moieties, or detectable labels are used, fluorescence photomicroscopy can be used to detect and record the results of in situ hybridization using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) *Science* 273:494; Roberts et al. (1999) *Genes Chrom. Cancer* 25:241; Fransz et al. (2002) *Proc. Natl. Acad. Sci. USA* 99:14584; Bayani et al. (2004) *Curr. Protocol. Cell Biol.* 22.5.1-22.5.25; Danilova et al. (2008) *Chromosoma* 117:345; U.S. Pat. No. 6,066,459; and FISH TAG™ DNA Multicolor Kit instructions (Molecular probes) for a review of methods for painting chromosomes and detecting painted chromosomes.

In certain exemplary embodiments, images of fluorescently labeled chromosomes are detected and recorded using a computerized imaging system such as the Applied Imaging Corporation CytoVision System (Applied Imaging Corporation, Santa Clara, Calif.) with modifications (e.g., software, Chroma 84000 filter set, and an enhanced filter wheel). Other suitable systems include a computerized imaging system using a cooled CCD camera (Photometrics, NU200 series equipped with Kodak KAF 1400 CCD) coupled to a Zeiss Axiophot microscope, with images processed as described by Ried et al. (1992) *Proc. Natl. Acad. Sci. USA* 89:1388). Other suitable imaging and analysis systems are described by Schrock et al., supra; and Speicher et al., supra.

In situ hybridization methods using probes generated by the methods described herein can be performed on a variety of biological or clinical samples, in cells that are in any (or all) stage(s) of the cell cycle (e.g., mitosis, meiosis, interphase, G0, G1, S and/or G2). Examples include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. Samples are prepared for assays of the invention using conventional techniques, which typically depend on the source from which a sample or specimen is taken. These examples are not to be construed as limiting the sample types applicable to the methods and/or compositions described herein.

In certain exemplary embodiments, probes include multiple chromosome-specific probes, which are differentially labeled (i.e., at least two of the chromosome-specific probes are differently labeled). Various approaches to multi-color chromosome painting have been described in the art and can be adapted to the present invention following the guidance provided herein. Examples of such differential labeling ("multicolor FISH") include those described by Schrock et al. (1996) *Science* 273:494, and Speicher et al. (1996) *Nature Genet.* 12:368). Schrock et al. describes a spectral imaging method, in which epifluorescence filter sets and computer software is used to detect and discriminate between multiple differently labeled DNA probes hybridized simultaneously to a target chromosome set. Speicher et al. describes using different combinations of 5 fluorochromes to label each of the human chromosomes (or chromosome arms) in a 27-color FISH termed "combinatorial multifluor FISH"). Other suitable methods may also be used (see, e.g., Ried et al., 1992, *Proc. Natl. Acad. Sci. USA* 89:1388-92).

Making Complementary Strands and Amplification

According to certain aspects, a nucleic acid sequence complementary to a nucleic acid template may be made by methods known to those of skill in the art including methods and materials from well-known amplification methods where a template nucleic acid is contacted with one or more primers, a polymerase and nucleotides under conditions to extend the primer along the template nucleic acid. This method is used if a duplex including the single strand template oligonucleotide is desired.

In general, "amplifying" includes the production of copies of a nucleic acid molecule, such as a nucleic acid molecule bound to an array or a nucleic acid molecule bound to a bead or a nucleic acid molecule in solution via repeated rounds of primed enzymatic synthesis. "In situ" amplification indicates that the amplification takes place with the template nucleic acid molecule positioned on a support or a bead, rather than in solution. In situ amplification methods are described in U.S. Pat. No. 6,432,360.

Varied choices of polymerases exist with different properties, such as temperature, strand displacement, and proofreading. Amplification can be isothermal, as described above and in similar adaptation such as multiple displacement amplification (MDA) described by Dean et al., Comprehensive human genome amplification using multiple displacement amplification, *Proc. Natl. Acad. Sci. U.S.A.*, vol. 99, p. 5261-5266. 2002; also Dean et al., Rapid amplification of plasmid and phage DNA using phi29 DNA polymerase and multiply-primed rolling circle amplification, *Genome Res.*, vol. 11, p. 1095-1099. 2001; also Aviel-Ronen et al., Large fragment Bst DNA polymerase for whole genome amplification of DNA formalin-fixed paraffin-embedded tissues, *BMC Genomics*, vol. 7, p. 312. 2006. Amplification can also cycle through different temperature regiments, such as the traditional polymerase chain reaction (PCR) popularized by Mullis et al., Specific enzymatic amplification of DNA in vitro: The polymerase chain reaction. *Cold Spring Harbor Symp. Quant. Biol.*, vole 51, p. 263-273. 1986. Variations more applicable to genome amplification are described by Zhang et al., Whole genome amplification from a single cell: implications for genetic analysis, *Proc. Natl. Acad. Sci. U.S.A.*, vol. 89, p. 5847-5851. 1992; and Telenius et al., Degenerate oligonucleotide-primed PCR: general amplification of target DNA by a single degenerate primer, *Genomics*, vol. 13, p. 718-725. 1992. Other methods include Polony PCR described by Mitra and Church, In situ localized amplification and contact replication of many individual DNA molecules, *Nuc. Acid. Res.*, vole 27, pages e34. 1999; emulsion PCR (ePCR) described by Shendure et al., Accurate multiplex polony sequencing of an evolved bacterial genome, *Science*, vol. 309, p. 1728-32. 2005; and Williams et al., Amplification of complex gene libraries by emulsion PCR, Nat. Methods, vol. 3, p. 545-550. 2006. Any amplification method can be combined with a reverse transcription step, a priori, to allow amplification of RNA.

Amplification methods useful in the present disclosure may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self-sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) J. Biol. Chem. 275:2619; and Williams et al. (2002) *J. Biol. Chem.* 277: 7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art.

In certain exemplary embodiments, methods for amplifying nucleic acid sequences include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self-sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach and PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 68-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 µL. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

Circularization and Rolling Circle Amplification

According to certain aspects, a single stranded nucleic acid may be circularized by methods known to those of skill in the art. According to one exemplary aspect, ssDNA can be circularized using ssDNA Circligase II (Epicentre #CL9025K) or other ssDNA ligase such as Circligase I (Epicentre #CL4115K), or by template-directed ligation using a combination of a dsDNA ligase (e.g. (T3, T4, T7 and other ds DNA ligases) with a bridge oligo (5'-ATGAG-GAACCCGGGGCAG-3'-PO$_4$). Chemical ligation methods have also been described (Dolinnaya et al., 1993; Kumar et al., 2007). Double stranded DNA may also be circularized by methods known to those of skill in the art. According to one aspect, dsDNA ligases may be used such as T3, T4, T7 and other ds DNA ligases.

According to one exemplary aspect, 10 pmol of ssDNA is circularized using Circligase II, according to the manufacturer's recommendation. Following the circularization, 20 units of Exonuclease I (Enzymatics #X801L) and 100 units of Exonuclease III (Enzymatics #X802L) are added to the reaction to digest any remaining linear template. Next, rolling circle amplification (RCA) is performed on the circular ssDNA template using a DNA polymerase with high processivity, strong displacement activity and low error rate. Aspects of the present disclosure include using rolling circle amplification to create a long strand nucleic acid. The long strand nucleic acid is a concatemer of the circular nucleic acid template used in the rolling circle amplification method. Rolling circle amplification methods are known to those of skill in the art and generally include the use of a circular nucleic acid template for DNA or RNA polymerases, which produce long, repeating copies of the circular sequence by a rolling circle process.

Rolling circle amplification methods are known to those of skill in the art and include Drmanac et al., Human genome sequencing using unchained base reads on self-assembling DNA nanoarrays, *Science*, vol. 327, p. 78-81 (2009). According to one exemplary aspect, 1 pmol of the circularized template is used with 20 units of phi29 DNA polymerase (Enzymatics #P702L). Additionally, dNTP (typically 1 mM) and a RCA primer (typically 1 pmol) are required. An exemplary RCA primer would have the form 5'-AATGAGGAACCCGGGGCA*G*C, where the * represents a phosphorothioate bond thereby indicating that the last 3' nucleotide bears a phosphorotioate bond, making the RCA less susceptible to phi29 3'->5' exonuclease activity. However, an exemplary RCA primer may not include such phosphorothioate bonds, especially if the polymerase used does not have 3'->5' exonuclease activity. Alternatively, an exemplary RCA primer may have phosphorothioate bonds on the 5' side of the RCA primer such as 5'-A*A*TGAGGAACCCGGGGCAGC. An annealing reaction is often performed before adding the phi29 (95° C. for 1 min, then 2 min cool down to 4° C.), to increase the RCA efficiency. Then the reaction is incubated at 30° C. for an hour (incubation periods between 15 min to 6 hours may also be used). Other temperatures can be used, since phi29 is active between 4° C. and 40° C. (with 90% diminished activity). Then, the reaction is cooled to 4° C. and the RCA products (referred to as Rolony) are recovered in cold PBS and can be stored at 4° C. until needed. Rolling circle amplification products, which are long strand nucleic acids of repeating sequences, prepared this way are stable for several months and can be separated into single stranded probes as described herein.

Methods of circularization and rolling circle amplification are described in Kool, Circular Oligonucleotides: New Concepts in Oligonucleotide Design, *Annu. Rev. Biophys. Biomol. Struct.* 1996. 25:1-28 and Diegelman, Generation of circular RNAs and trans-cleaving catalytic RNAs by rolling transcription of circular DNA oligonucleotides encoding hairpin ribozymes, *Nucleic Acids Research,* 1998, Vol. 26, No. 13, 3235-3241 each of which are hereby incorporated by reference herein in their entireties for all purposes.

Cleavage of Long Strand Concatemers Made by RCA

According to certain aspects, nucleic acid products of rolling circle amplification are cleaved or otherwise separated into a plurality of smaller nucleic acid sequences using methods known to those of skill in the art and including the discussion of cleavable moieties provided herein. For example, nucleic acid products of rolling circle amplification described herein include a plurality of cleavable moieties which may be cleaved using reagents and conditions described herein and known to those of skill in the art. For example, nucleic acid products of rolling circle amplification described herein include a plurality of RNA or DNA polymerase recognition sites. If a DNA polymerase recognition site is used, then an RNA sequence can hybridize with the DNA polymerase recognition sequence and an RNAse that recognizes DNA/RNA hybrids can be used to cleave the nucleic acid products of rolling circle amplification into smaller nucleic acid sequences or probes. Likewise, if an RNA polymerase recognition site is used, then a DNA sequence can hybridize with the RNA polymerase recognition sequence and an RNAse that recognizes DNA/RNA hybrids can be used to cleave the nucleic acid products of rolling circle amplification into smaller nucleic acid sequences or probes.

In addition, the nucleic acid products of rolling circle amplification may be sheared into smaller nucleic acid fragments or oligonucleotides using available blending or shearing devices known to those of skill in the art. According to this aspect, mechanical forces are used to break apart the long chain nucleic acids and result in a plurality of smaller nucleic acids or oligonucleotides useful as probes.

In addition, nucleic acid products of rolling circle amplification are cleaved into a plurality of smaller nucleic acid sequences using ribozyme methods known to those of skill in the art as described in Diegelman, *Nucleic Acids Research,* 1998, Vol. 26, No. 13, 3235-3241 and incorporated by reference herein.

The contents of all references, patents and published patent applications cited throughout this application are hereby incorporated by reference in their entirety for all purposes.

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A plurality of nucleic acid probes in the form of a single stranded nucleic acid concatamer of repeating nucleic acid probe sequences wherein each nucleic acid probe sequence comprises
    a polymerase recognition site at one end, a first nucleic acid sequence complementary to a target sequence, and a label addition site
    at the other end,
    and further comprising a hybridized oligonucleotide at the polymerase recognition site to form a hybrid that is recognizable by an endonuclease.

2. The nucleic acid probes of claim 1 wherein the single stranded nucleic acid concatamer is DNA.

3. The nucleic acid probes of claim 1 wherein the single stranded nucleic acid concatamer is RNA.

4. The nucleic acid probes of claim 1 wherein the polymerase recognition site is an RNA polymerase recognition site.

5. The nucleic acid probes of claim 1 wherein the polymerase recognition site is a DNA polymerase recognition site.

6. The nucleic acid probes of claim 1 wherein the label addition site comprises a sequence complementary to a secondary probe including a label.

7. The method of claim 1 wherein the hybridized oligonucleotide is DNA and the polymerase recognition site is DNA to produce a DNA/DNA hybrid recognizable by the endonuclease.

8. The method of claim 1 wherein the hybridized oligonucleotide is DNA and the polymerase recognition site is RNA to produce a DNA/RNA hybrid recognizable by the endonuclease.

9. The method of claim 1 wherein the hybridized oligonucleotide is RNA and the polymerase recognition site is DNA to produce a RNA/DNA hybrid recognizable by the endonuclease.

10. The method of claim 1 wherein the hybridized oligonucleotide is RNA and the polymerase recognition site is RNA to produce a RNA/RNA hybrid recognizable by the endonuclease.

* * * * *